(12) United States Patent
Werblin

(10) Patent No.: US 9,398,949 B2
(45) Date of Patent: Jul. 26, 2016

(54) INTRAOCULAR LENS SYSTEM

(75) Inventor: Theodore P. Werblin, Princeton, WV (US)

(73) Assignee: EMMETROPIA, INC., Princeton, WV (US)

(*) Notice: Subject to any disclaimer, the term of this patent is extended or adjusted under 35 U.S.C. 154(b) by 803 days.

(21) Appl. No.: 12/910,405

(22) Filed: Oct. 22, 2010

(65) Prior Publication Data

US 2011/0040378 A1 Feb. 17, 2011

Related U.S. Application Data

(63) Continuation-in-part of application No. 12/499,613, filed on Jul. 8, 2009, now Pat. No. 8,066,769, which is a continuation-in-part of application No. 12/000,364, filed on Dec. 12, 2007, now Pat. No. 7,811,320, which is a continuation-in-part of application No. 11/698,875, filed on Jan. 29, 2007, now Pat. No. 8,066,768.

(51) Int. Cl.
A61F 2/16 (2006.01)

(52) U.S. Cl.
CPC ....... *A61F 2/1648* (2013.01); *A61F 2002/1682* (2015.04); *A61F 2002/1686* (2013.01); *A61F 2250/0039* (2013.01)

(58) Field of Classification Search
CPC ... A61F 2/1613; A61F 2/1694; A61F 2/1629; A61F 2/16; A61F 2/1648; A61F 2/1635
USPC .............. 623/4.1, 6.32, 6.34, 6.43, 6.49
See application file for complete search history.

(56) References Cited

U.S. PATENT DOCUMENTS

| 2,036,379 A | 4/1936 | Woodward |
| 2,039,144 A | 4/1936 | Burgess |
| 2,168,925 A | 8/1939 | Hewes et al. |
| 2,354,586 A | 7/1944 | Fischer |

(Continued)

FOREIGN PATENT DOCUMENTS

| DE | 707212 | 5/1941 |
| DE | 3428895 A1 | 2/1986 |

(Continued)

OTHER PUBLICATIONS

Wikipedia, "Presbyopia", The Free Encyclopedia, pp. 1-4, Oct. 30, 2006.

(Continued)

*Primary Examiner* — David H Willse
*Assistant Examiner* — Tiffany Shipmon
(74) *Attorney, Agent, or Firm* — Arent Fox LLP

(57) ABSTRACT

A multi-component intraocular lens implanted in an optical system of a human eye, includes one or more removable components. One component acts as a base lens and another component acts as the front lens. A front lens formed from two integral optical portions may be milled with tabs to establish an axial orientation of the front lens. The front lens may have a different diameter than the base lens. The base lens may have sharp or angled edges and the front lens may have rounded edges. Non-optical portions of the intraocular lens system may be manufactured from a material that is capable of releasing a pharmacological agent. A flange may be fused with the base lens to allow the front lens to engage with the base lens.

15 Claims, 32 Drawing Sheets

(56) References Cited

U.S. PATENT DOCUMENTS

| | | | |
|---|---|---|---|
| 2,798,373 A | 7/1957 | Harza | |
| 2,806,809 A | 9/1957 | Schuh | |
| 3,128,576 A | 4/1964 | Bradley | |
| 3,194,130 A | 7/1965 | Guntert | |
| 3,200,482 A | 8/1965 | Brown | |
| 3,265,556 A | 8/1966 | Hungerford et al. | |
| 3,269,282 A | 8/1966 | Beesley et al. | |
| 3,458,870 A | 8/1969 | Stone, Jr. | |
| 3,925,825 A * | 12/1975 | Richards et al. | 623/6.41 |
| 3,945,054 A | 3/1976 | Fedorov et al. | |
| 4,010,496 A | 3/1977 | Neefe | |
| 4,240,163 A | 12/1980 | Galin | |
| 4,373,218 A | 2/1983 | Schachar | |
| 4,402,579 A | 9/1983 | Poler | |
| 4,575,373 A | 3/1986 | Johnson | |
| 4,585,456 A | 4/1986 | Blackmore | |
| 4,585,457 A | 4/1986 | Kalb | |
| 4,636,212 A | 1/1987 | Posin et al. | |
| 4,655,770 A | 4/1987 | Gupta et al. | |
| 4,685,921 A | 8/1987 | Peyman | |
| 4,685,922 A | 8/1987 | Peyman | |
| 4,731,078 A | 3/1988 | Stoy et al. | |
| 4,769,035 A | 9/1988 | Kelman | |
| 4,778,463 A | 10/1988 | Hetland | |
| 4,787,903 A | 11/1988 | Grendahl | |
| 4,834,754 A | 5/1989 | Shearing | |
| 4,838,266 A | 6/1989 | Koziol et al. | |
| 4,842,601 A | 6/1989 | Smith | |
| 4,863,466 A | 9/1989 | Schlegel | |
| 4,892,543 A * | 1/1990 | Turley | 623/6.13 |
| 4,932,971 A | 6/1990 | Kelman | |
| 4,950,289 A | 8/1990 | Krasner | |
| 5,066,301 A | 11/1991 | Wiley | |
| 5,085,013 A | 2/1992 | Ascosi et al. | |
| 5,098,444 A | 3/1992 | Feaster | |
| 5,133,748 A | 7/1992 | Feaster | |
| 5,171,267 A | 12/1992 | Ratner et al. | |
| 5,196,027 A | 3/1993 | Thompson et al. | |
| 5,222,981 A | 6/1993 | Werblin | |
| 5,288,293 A | 2/1994 | O'Donnell, Jr. | |
| 5,366,502 A | 11/1994 | Patel | |
| 5,628,798 A | 5/1997 | Eggleston et al. | |
| 5,728,155 A | 3/1998 | Anello et al. | |
| 5,777,719 A | 7/1998 | Williams et al. | |
| 5,814,103 A | 9/1998 | Lipshitz et al. | |
| 5,892,617 A | 4/1999 | Wallace | |
| 5,943,117 A | 8/1999 | Van de Velde | |
| 5,968,094 A * | 10/1999 | Werblin et al. | 623/6.34 |
| 6,113,633 A | 9/2000 | Portney | |
| 6,193,750 B1 * | 2/2001 | Cumming | 623/6.43 |
| 6,254,637 B1 | 7/2001 | Lee et al. | |
| 6,255,338 B1 | 7/2001 | Duncan et al. | |
| 6,413,276 B1 | 7/2002 | Werblin | |
| 6,524,340 B2 | 2/2003 | Israel | |
| 6,551,354 B1 | 4/2003 | Ghazizadeh et al. | |
| 6,599,317 B1 * | 7/2003 | Weinschenk et al. | 623/6.34 |
| 6,786,927 B2 * | 9/2004 | Pallikaris et al. | 623/6.13 |
| 6,991,651 B2 | 1/2006 | Portney | |
| 7,008,449 B2 | 3/2006 | Willis et al. | |
| 7,097,660 B2 | 8/2006 | Portney | |
| 7,300,464 B2 | 11/2007 | Tran | |
| 7,316,713 B2 * | 1/2008 | Zhang | 623/6.37 |
| 7,591,849 B2 * | 9/2009 | Richardson | 623/6.47 |
| 2001/0001836 A1 * | 5/2001 | Cumming | 623/6.37 |
| 2001/0044657 A1 * | 11/2001 | Kellan | 623/6.51 |
| 2002/0161436 A1 | 10/2002 | Portney | |
| 2003/0204254 A1 | 10/2003 | Peng et al. | |
| 2004/0117013 A1 | 6/2004 | Schachar | |
| 2005/0125058 A1 | 6/2005 | Cumming et al. | |
| 2006/0047339 A1 | 3/2006 | Brown | |
| 2006/0216329 A1 * | 9/2006 | Peyman | 424/428 |
| 2008/0215147 A1 | 9/2008 | Werblin | |
| 2008/0243236 A1 * | 10/2008 | Dancu | 623/1.41 |
| 2009/0076603 A1 | 3/2009 | Avery et al. | |

FOREIGN PATENT DOCUMENTS

| | | | |
|---|---|---|---|
| EP | 0 269 198 A1 | 6/1988 | |
| EP | 0 435 525 B1 | 7/1991 | |
| FR | 2 666 735 A1 | 3/1992 | |
| FR | WO9717915 * | 5/1997 | A61F 2/16 |
| JP | H08103457 * | 4/1996 | A61F 2/16 |
| WO | WO 91/06259 A1 | 5/1991 | |
| WO | WO 92/20302 A1 | 11/1992 | |

OTHER PUBLICATIONS

Ernani Serpa Junior, et al.,"Comparison of PMMA, foldable silicone and foldable acrylic hydrophobic intraocular lenses in combined phacoemulsification and trabeculectomy", Arq Bras Oftalmol, 2005; 68 (1): 29-35.

Cyw Khng et al., "The IOL flip: rescue for foldable lens implantation gone wrong", The BMJ Interview-BJO Online Journals, Oct. 30, 2006, pp. 1-5.

Cyw Khng, et al., "The IOL flip: rescue for fordable lens implantaion gone wrong", BJO Online Journals, Br. J. Ophthalmol 2003, 87, pages 656-657 doi: 10.1136/bjo.87.5.656.

Theodore P. Werblin, "Why Should Refractive Surgeons Be Looking Beyond the Cornea?", Barraquer Lecture 1998, Journal of Refractive Surgery vol. 15 May/Jun. 1999, pp. 359-376.

Theodore P. Werblin et al., "Epikeratophakia" The surgical correction of aphakia. III. Preliminary results of a prospective clinical trial, 99 Arch. Opth., pp. 1957-1960 (1981).

Theodore P. Werblin et al., "Hydrogel Keratophakia: Measurement of Intraocular Pressure," vol. 11, No. 4 CLAO Journal, pp. 354-357 (Oct. 1985).

Theodore P. Werblin et al.,"Refractive Corneal Surgery: The Use of Implantable Alloplastic Lens Material", 11 Austrial Journal of Opthalmology, pp. 325-331 (1983).

Theodore P. Werblin, "Lamellar Refractive Surgery: Where Have We Been and Where Are We Going?" vol. 5, No. 3, Refractive and Corneal surgery, pp. 167-176 (Jan. 1989).

Perry S. Binder et al. Hydrogel Refractive Keratoplasty. Lens Removal, and Exchanges vol. 2, Cornea 2 at pp. 119-125.

Theodore P. Werblin et al., Epikeratophakia: The surgical correction of aphakia. II. Preliminary results in a non-human primate model; 1(3) Curr. Eye Res., pp. 131-137; 1981.

* cited by examiner

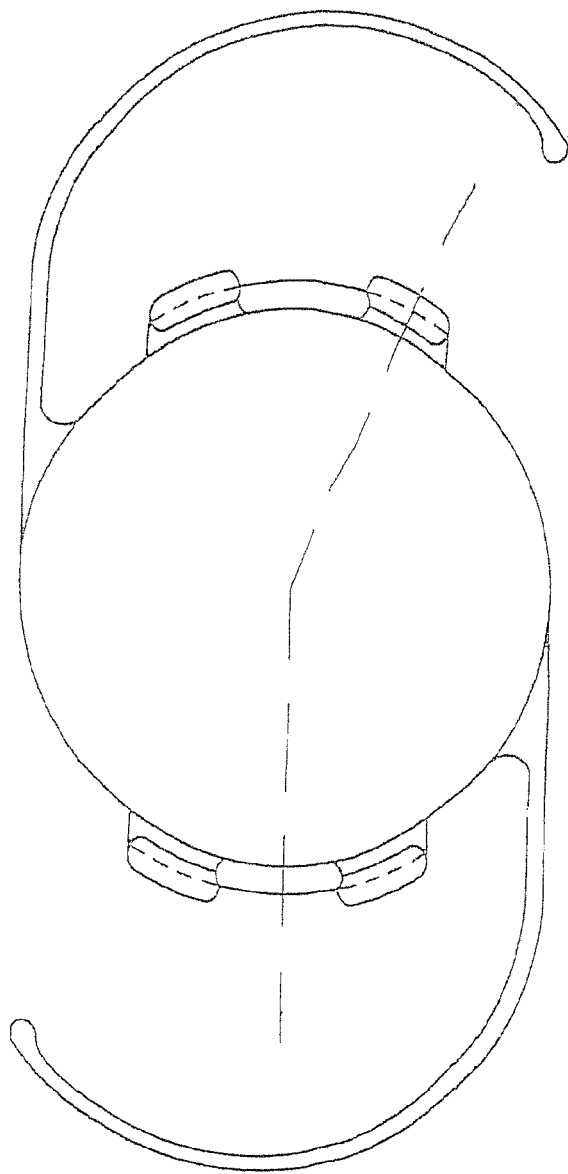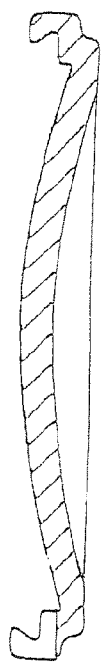
FIG. 4A (RELATED ART)
FIG. 4B (RELATED ART)

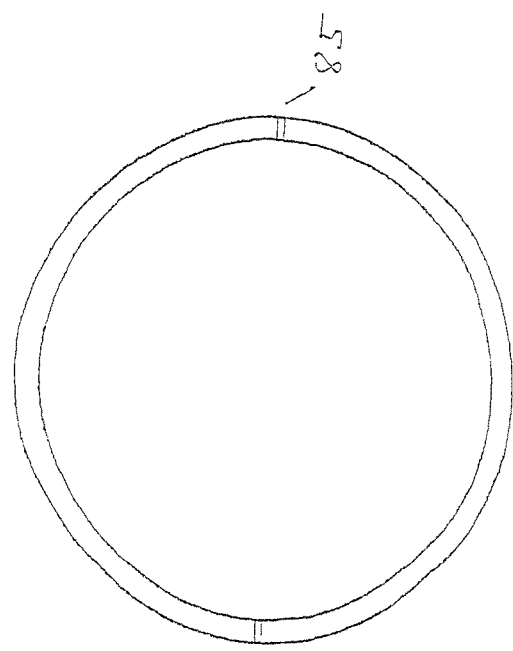
FIG.5A (RELATED ART)
FIG.5B (RELATED ART)

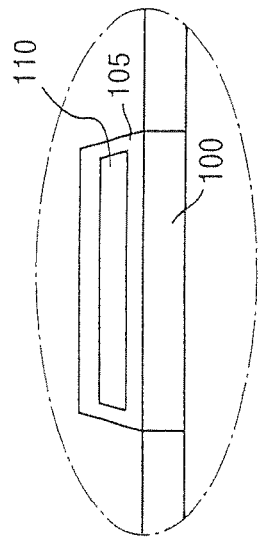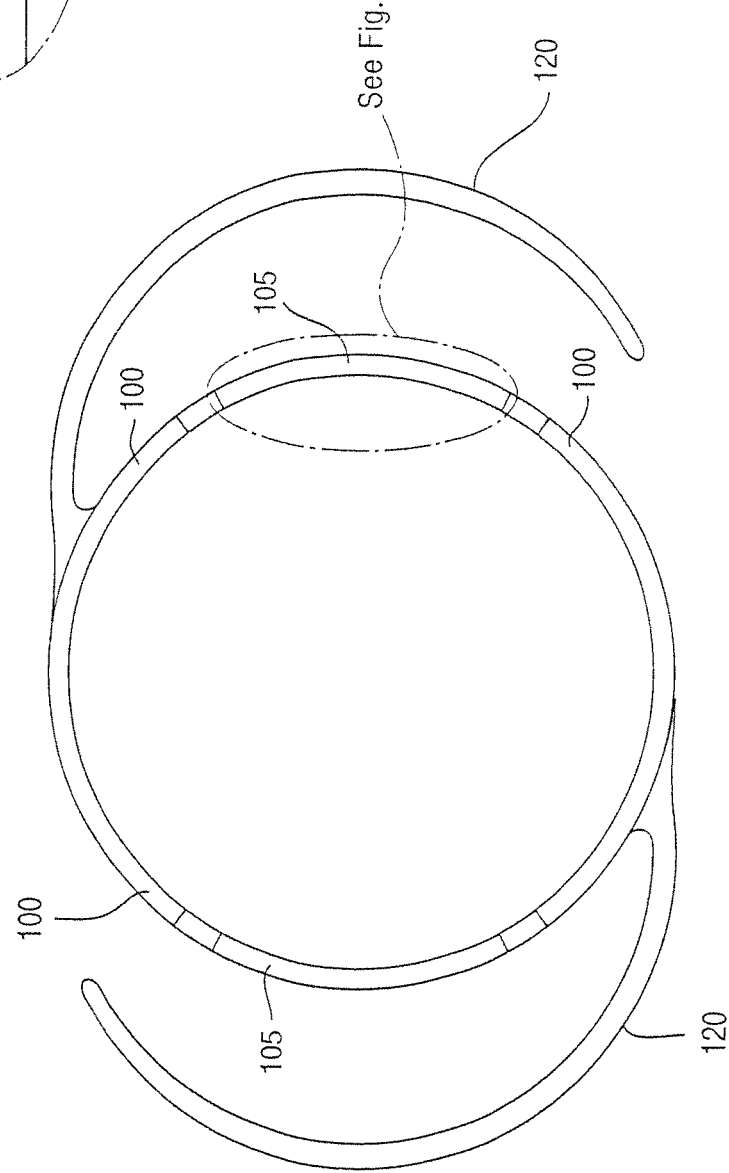
Fig. 12B (RELATED ART)
Fig. 12A (RELATED ART)

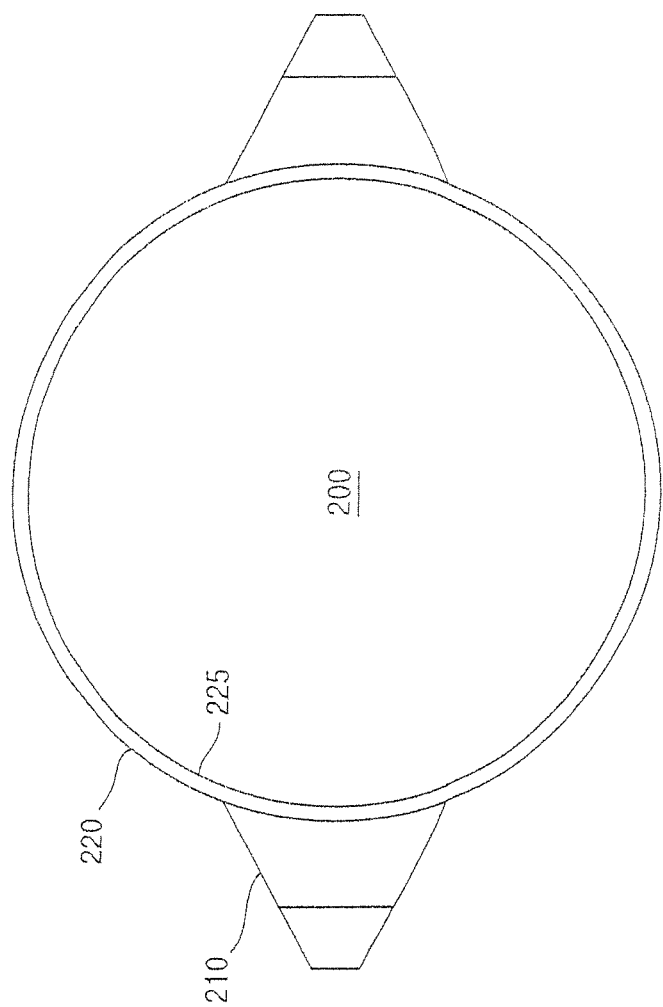
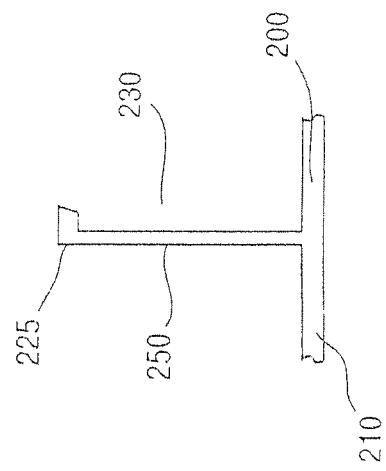
Fig. 14A (RELATED ART)
Fig. 14B (RELATED ART)

| 3000 |
|---|
| 2000 |
| 4000 |
| 1000 |

| 2000 |
|---|
| 3000 |
| 4000 |
| 1000 |

| 4000 |
|---|
| 2000 |
| 3000 |
| 1000 |

| 3000 |
|---|
| 2000 |
| 4000 |
| 7000 |
| 6000 |
| 5000 |
| 1000 |

# INTRAOCULAR LENS SYSTEM

CROSS-REFERENCE TO RELATED APPLICATION

This is a continuation-in-part application of application Ser. No. 12/499,613, filed Jul. 8, 2009, which is a continuation-in-part application of application Ser. No. 12/000,364, filed Dec. 12, 2007, which is a continuation-in-part application of application Ser. No. 11/698,875, filed Jan. 29, 2007.

BACKGROUND OF THE INVENTION

1. Field of the Invention

This invention relates to a method for correcting the optical system of an eye using an intraocular lens system. Particularly, this invention relates to a method of correcting focusing abnormalities and optical aberrations measured by wave front or similar technology to quantify optical aberrations in the optical system of the eye, using a laser, or other apparatus and/or methods of fabricating or modifying a lens, for the optical system of an eye having a foldable, interchangeable intraocular lens system provided therein.

2. Description of Related Art

The field of refractive surgery has evolved rapidly during the past few decades. Current procedures and methods used by refractive surgeons may not satisfy the total refractive needs of the patient. Particularly, the most commonly performed refractive surgical procedures, such as, for example, cataract extraction with intraocular lens implantation, in addition to the most recently popularized corneal refractive surgical procedures, such as eximer laser photoblation, exhibit limitations. One reason for the limitations is the lack of post-operative refractive accuracy. The lack of post-operative refractive accuracy renders the commonly known refractive surgical procedures uncompetitive with currently available non-surgical alternatives for patients, for example, glasses and contact lenses. Further, because refractive surgery requires local or general anesthesia and incisions into the eye, a need exists for decreasing the trauma resultant from the surgery.

Recently, a need has arisen for efficient treatment of presbyopia, or the diminished power of accommodation of the eye. Presbyopia is a condition which typically affects a large number of people as they age, with the severity of the condition varying depending on the person. Difficulties arise in treating presbyopia because typically once a person manifests symptoms of presbyopia, the symptoms worsen as the person ages. As a person's condition worsens, a different, usually more powerful, lens is required to correct the condition. Conventional techniques for replacing an intraocular lens each time the patient's vision deteriorates do not always present a practical or cost-effective approach. Recent developments in the field of refractive surgery have made intraocular treatment of presbyopia a feasible course of treatment for those patients that desire or need improved vision, however a need exists for more precise techniques and devices for use in refractive intraocular surgery.

Patients suffering from eye trauma or other eye afflictions may have the iris or other portions of the eye distorted, destroyed, or discolored. Currently, such patients are typically prescribed cosmetic contact lenses. Cosmetic intraocular lens replacement is emerging as a viable alternative, however a need exists for more efficient intraocular lens replacement in order to minimize eye trauma and establish cosmetic intraocular lens replacement as a safe and effective alternative to cosmetic contact lenses and other non-surgical treatments. As surgical techniques become more effective, safer, and less painful, patients may choose to have elective lens replacement surgery to change the color, structure, or shape of their eyes. By providing a minimally invasive method for lens replacement as described in an embodiment herein, the surgeon is able to limit the drawbacks of the procedure.

Current procedures and methods for refractive surgery require the performing surgeon to execute the procedure with a high level of skill and experience. Currently, methods and procedures for carrying out refractive surgery involving intraocular lenses generally require direct visualization of the intraocular lens assembly within the eye. Such visualization, although not outside the scope of a surgeon skilled in the art, increases the degree of difficulty of the procedure, thus increasing the chance that a surgical error or other problem will arise in the surgical procedure, leading to unwanted complications. Thus, a need exists for intraocular lens assemblies and systems whose structures provide less complex methods of insertion into and extraction from the eye.

Currently, refractive cataract surgeons performing the most common refractive surgical procedure, i.e., routine cataract surgery, obtain refractive accuracies in a +/−0.75 to +/−1.00 diopter (D) range. However, the industry has established goals of obtaining refractive accuracies in the +/−0.25 D range. Therefore, there is a need in the industry to provide a more accurate alternative to the current procedure. Furthermore, analyses of current corneal refractive technologies indicate the presence of a significant amount of preexisting or naturally occurring post-operative, as well as preoperative, image distortion (optical aberration) or degradation, particularly under low light conditions, such as when driving at night.

Due to the practical limits of performing intraocular surgery, as well as the biological and physical behavior of the human eye during and after various types of intraocular surgery, predictability at the +/−0.25 D accuracy level with a single surgical procedure is difficult to achieve as a practical matter. Furthermore, factors such as biometry errors, variable wound healing, and capsular contraction around the intraocular lenses contribute to decreasing the likelihood of achieving the desired refractive accuracy. Accordingly, practitioners in the industry have found that an adjustable intraocular lens (IOL), multi-component (MC-IOL), or compound (C-IOL), following lens extraction surgery provides a plurality of desirable options for refractive surgeons and patients.

An adjustable IOL allows fine tuning of the initial refractive result by exchanging at least one of the optical elements of the lens implant. As a result, accuracies in the +/−0.25 D range are readily attainable. Furthermore, patients are provided with an opportunity to exchange the "old" lens components with new and hopefully more accurate components. Such an objective is obtainable if the surgeon has an effective, efficient, and safe method of performing lens element exchanges. Additionally, months and/or years after the refractive surgical procedure, if the optical properties of the inserted IOL, for example, the multifocality, become problematic, the surgeon should have the ability to safely exchange the undesirable optical elements of the IOL to correct any optical aberrations that the patient will not or cannot tolerate.

In 1990, the inventor of this application developed a multi-component intraocular lens, i.e., MC-IOL (FIG. 1), for use following clear lens or refractive cataract surgery, wherein the optical properties of the MC-IOL can be modified at any post-operative time. The base intraocular lens component of the MC-IOL is shown in FIG. 1. The mid lens attaches to the top of the base lens and holds the third component of the MC-IOL, the top lens, in place.

The base intraocular lens 10 and the mid lens 20 each have securing flanges 16, 18 and 20, 24, respectively, extending therefrom. The MC-IOL also comprises at least one top lens 30, as illustrated in FIG. 1. The top lens 30 is positioned on top of the mid lens 20. See FIGS. 1-2.

The MC-IOL also includes projections (or haptics) 11 and 13 which securely hold the MC-IOL in the tissue of the human eye. The above-described structure permits the base intraocular lens 10 to form a platform upon which the mid lens 20 is placed, and to hold the top lens 30. During routine cataract surgery, the MC-IOL replaces the crystalline lens of the human eye. Once a patient's eye has healed after such a surgery, the surgeon reenters the eye and replaces, if necessary, and more than once, the top lens 30 and the mid lens 20 to modify the optical characteristics of the eye until the desired levels for each optical characteristic are attained.

FIGS. 3A-3B illustrate an assembled compound intraocular lens, i.e., C-IOL, used with a preexisting lens within the human eye. The C-IOL has two components similar to the mid lens (FIGS. 4A-4B) and the top lens (FIGS. 5A-5B) components of the MC-IOL. FIG. 5A also illustrates the axis orientation mark 85 used in some embodiments of MC-IOL lenses to aid in positioning and orienting the lens. The preexisting lens can be the crystalline lens of the eye with the C-IOL placed in the sulcus (FIG. 6) or in the anterior chamber angle (FIG. 7) of the eye's optical system. However, the C-IOL can also be used with a conventional IOL, as well as with an accommodating IOL, and mounted in the sulcus (FIG. 8), in the anterior chamber angle (FIG. 9), in the anterior chamber with posterior chamber fixation (FIG. 10) or in the anterior chamber with iris fixation (FIG. 11). Thus, a surgeon modifies the optical characteristics of the optical system of the eye by using the mid and top lenses in tandem with the preexisting conventional IOL implant or crystalline lens of the eye.

The C-IOL and MC-IOL provide numerous enhanced features. For example, the C-IOL and MC-IOL can each be structured as a monofocal or multifocal optical system, correct astigmatism, as well as comprise ultraviolet light-absorbing, tinted, or other such chemically treated materials.

It should be understood that there are various reasons why an adjustable MC-IOL or C-IOL is more desirable than a single component implant. In order to achieve all the permutations and combinations of the astigmatism, multifocality, and spherical correction needed to achieve emmetropia would take an inventory of over ten thousand lenses, whereas with the MC-IOL (multiple components) concept, an inventory of about one hundred components would be necessary. With anterior chamber lenses, progressive encapsulation or engulfment of the lens haptics by uveal tissue in the angle often occurs 1-2 years post-operatively. The engulfment typically makes the removal of the lenses and their haptics more difficult. Exchange of iris fixated anterior chamber lenses does not typically guarantee precise position or orientation. Posterior chamber lenses similarly cannot be removed because of posterior capsule fibrosis. Easy removal and exchangeability is critical for any customized emmetropic system, which can be provided by a specially designed multicomponent lens system.

Therefore, based on the above, a MC-IOL having three elements rather than one permits refractive customization and adjustability for all refractive errors, as well as for all patients, while using a minimal number of lens elements or parts and requiring little customization on the part of the manufacturer. Thus, it has become very important in the refractive surgery art to be able to individualize and/or customize surgery such that the surgeon can easily and safely, as well as accurately, modify the refractive power of an intraocular lens implant.

For example, U.S. Pat. No. 5,288,293 to O'Donnell, Jr. discloses a method of modifying a single IOL. O'Donnell suggests that the refractive power of a single IOL may be varied before implantation so that the changes can be made in situ by the ophthalmologist after determining the extent of correction required to improve the vision of the patient before the lens is made. However, the surgical implantation procedure itself may create additional optical aberrations which cannot be anticipated preoperatively and thus the primary lens implant cannot account for these optical aberrations.

As such, it may be argued that if a lens can be modified before being implanted, as suggested by O'Donnell, Jr., it should be possible to modify the implanted lens by removing the implanted lens, modifying the lens, and then reimplanting the modified lens into the optical system of the eye. However, the design of current intraocular lenses typically makes such a procedure difficult and impractical. Furthermore, after a period of time with normal healing, it becomes physically dangerous and/or nearly impossible for the patient to have the implanted lens removed once the eye tissue takes hold on the capsular fixation holes of the lens. Therefore, such an argument is not realistic, practical, or safe. A single component intraocular lens, which in general is not designed to be removed and with only two optical surfaces, cannot accurately allow for compensation of sphere, cylinder, cylindrical axis, and all forms of optical aberrations that may be discovered after the initial implantation. However, the MC-IOL typically will have four removable optical surfaces which can compensate for these optical properties.

The inventor of this application invented the previously discussed MC-IOL and C-IOL that are designed specifically to permit the easy exchange of optical elements at a post-operative period without risk to the human eye or to the patient, beyond the risk of ordinary intraocular surgery. The easy exchangeability of optical elements is critical because the actual surgery of implanting the lens in the first place, as well as variances in the manner in which the eye heals after implantation, potentially create distortions which may not stabilize for several months after the operation. Therefore, the ability to measure and to compensate for the distortion(s) optimally takes place several months after surgery and cannot typically be predicted prior thereto. Since the same surgical wound is used for both the primary and secondary operations, additional distortion due to wound healing would not be anticipated as a result of the second operation.

Furthermore, the ability to exchange optical elements of a MC-IOL or C-IOL can be economical compared to removing, modifying, and re-implanting a single component lens, as well as easier to perform.

The MC-IOL has four surfaces available for modification, two plano and two convex. Preferably, the modification is made only to the plano surfaces to avoid interfering with the convex side which may already be used for correction of astigmatism (cylinder) or used as a multifocal lens surface. The same preference applies to the CIOL, which has two surfaces available for modification, one plano and the other convex.

The inventor of this application also developed a system for correcting optical aberrations in the MC-IOL, as described, for example, in U.S. Pat. No. 6,413,276, for conducting measurements to determine any residual or new aberrations present in an operated eye after the biological healing parameters have stabilized, as well as to correct any errors in sphere, cylinder, or cylindrical axis, and for modifying one, two, or more existing lens elements within the implanted optical system based on the conducted measurements.

In conventional multi-component intraocular lens designs, the surgical procedure required to implant the intraocular lens components requires a high level of surgeon skill. For example, implantation of the removable component of the lens requires the surgeon to directly visualize the placement of the lens in order to match the notches with the flanges. Further, removal of the removable lens component requires a special forceps tool for grabbing the base lens, and releasing the tabs holding the sandwich and cap lens together with the base lens (see, for example, the system described in U.S. Pat. No. 5,968,094).

Historically intraocular lens systems used a rigid one piece poly methyl methacrylate (PMMA) lens. The PMMA lens is approximately six millimeters in diameter. Because the PMMA lens is rigid, insertion of the PMMA intraocular lens generally requires a seven or eight millimeter incision to be inserted into the eye. In contrast, a flexible or foldable lens can be manipulated and compacted to a much smaller size. Once compacted, the multi-component intraocular lens can be delivered using a relatively smaller incision, for example, about three millimeters or less. By using a smaller incision, the patient reaps optical and practical benefits. From an optical standpoint, any time incisions are made to the cornea, the cornea loses some of its natural globularity due to imperfections caused by the incisions and the resultant trauma. The imperfections in the cornea lead to induced astigmatism, or optical aberrations caused by irregularities in the shape of the cornea. By minimizing the size of the corneal incision, a surgeon may also minimize the amount of induced astigmatism. Even though the three-component design simplifies the process of correcting induced astigmatism, minimizing the amount of induced astigmatism remains a primary goal for all intraocular surgeries.

As a practical matter, by making a smaller incision, the surgeon reduces the amount of actual trauma to the eye, thus reducing the occurrence of complications and decreasing the time for recovery. These advantages are further realized if the surgeon is able to perform the intraocular surgery using an incision small enough to heal without the use of stitches, wherein the incision is small enough to allow the eye's natural ocular pressure to hold the incision together during the healing process.

The inventor's application Ser. No. 11/698,875 overcame the above-described drawbacks of the related art. FIGS. 12-16 illustrate the invention disclosed in the '875 patent application.

For example, FIG. 12A shows a top or plan view of an intraocular foldable base lens 100, which is similar to the MC-IOL base lens illustrated in FIG. 3. The base lens 100 attaches to the eye by at least one haptic 120 and while the base lens 100 in FIG. 12A can be secured to the eye by at least one haptic, it is preferable that at least two haptics 120 be used. As shown in FIG. 12A, each haptic 120 extends outward from the base lens 100, and is tilted from between 10 to 20 degrees, in either direction, relative to a plane taken across the base lens, preferably having a 15 degree positive tilt.

As shown in FIG. 12B, as well as later in FIG. 24, the base lens 100 (1000, FIG. 24) can also include one or more flanges 105 (1005, FIG. 24) disposed on and extending outwardly away from the body of the base lens 100 (1000, FIG. 24). Each flange 105 (1005, FIG. 24) can also have a slot 110 (1100, FIG. 24) designed or configured to receive or accept an assembly of a top lens 300 (3000, FIG. 24) and a mid lens 200 (2000, FIG. 24) therein. Each flange 105 (1005, FIG. 24) and slot 110 (1100, FIG. 24) is an essential feature to the design of base lens 100 (1000, FIG. 24). The MC-IOL concept allows for adjustments or enhancement operations, beyond its use in primary cataract, clear lens, surgery to compensate for any miscalculation or any biological variability or any change in the condition of the eye over time after the primary operation. In order for these surgical adjustments to be workable, the surgeon must have easy access to the front lens assembly 200, 300 (2000, 3000 FIG. 24). To assure this, the front lens assembly 200, 300 (2000, 3000 FIG. 24) must be left out of the capsule, in the sulcus. On the other hand, the base lens 100 (1000, FIG. 24) is left in the capsule. In the primary surgery after the MC-IOL is inserted and the edges of the capsule are placed between the haptics 210, see FIG. 14A (2100, FIG. 24) of the front lens assembly 200, 300 (2000, 3000 FIG. 24) and the base lens 100 (1000, FIG. 24), the vertically extending flanges 105 (1005, FIG. 24) and their corresponding slots 110 (1100, FIG. 24) allow a space between the haptics 210, see FIG. 14A (2100, FIG. 24) of the front lens assembly 200, 300 (2000, 3000 FIG. 24) and the base lens 100 (1000, FIG. 24) so that a special instrument, referred to as a capsule snare, allows the surgeon to place the front lens assembly haptic 210 (2100, FIG. 24) above the edges of the capsule (6-7 mm capsulorrhexis necessary in the primary surgery) thus capturing the capsule between the haptics 210 and 120 (2100 and 1200 of FIG. 24). The remaining capsule "cellophane wraps" around the edges, the haptics 120 (1200, FIG. 24) and the edges of the base lens 100 (1000, FIG. 24) during the healing process after the cataract, clear lens, surgery. The "cellophane wrapping" makes it extremely difficult and dangerous for the surgeon to gain access to any surface of the base lens 100 (1000, FIG. 24) after the primary surgery heals, which is necessary for enhancement operations. The vertically extending flanges 105 (1005, FIG. 24) and corresponding slots 110 (1100, FIG. 24) position the front lens assembly 200, 300 (2000, 3000, FIG. 24) in front of or away from the "cellophane wrapped" posterior capsule, that is, in the sulcus, making surgical removal and replacement of the front lens assembly 200, 300 (2000, 3000, FIG. 24), very safe and technically simple.

Put another way, the flanges 105 (1005, FIG. 24) and slots 110 (1100, FIG. 24) are necessary features of the MC-IOL design to assure easy removal and replacement of the front lens assembly 200, 300 (2000, 3000, FIG. 24) during an enhancement operation. Without the vertical flange 105 (1005, FIG. 24), the edges and haptics 210 (2100, FIG. 24) are inaccessible to the surgeon due to capsule contracture around the edges and haptics 120 (1200, FIG. 24) of the base lens 100 (1000, FIG. 24), that is, the normal healing process. The structural configuration of the flange 105 (1005, FIG. 24) and corresponding slot 110 (1100, FIG. 24) position the base lens assembly 200, 300 (2000, 3000, FIG. 24) in front of the capsule, in the sulcus, which allows or facilitates easy access for the surgeon to remove and the replace the front lens assembly 200, 300 (2000, 3000, FIG. 24) during an enhancement operation any time during the life of the patient after the primary operation has healed.

The base lens in FIG. 13 is similar to the base lens 100 (FIGS. 12A-12B), except for a groove 130 being defined therein that extends along the entire outer periphery, and a plurality of attachment points 140, which serve to attach the optical region 150 to the base lens.

The foldable MC-IOL disclosed in the inventor's '875 application includes two or more additional refractive components, i.e., a top lens 300 and a mid lens 200. The mid lens 200, which typically allows spherical adjustments, is illustrated in FIGS. 14A-14B, while the top lens 300 (FIG. 15) carries the astigmatic correction and has an orientation projection 305. The mid lens 200 may include at least one projection 210 extending away from the body of the mid lens 200 and may have varying lengths depending on the shape and number of projections. The mid lens 200 also includes a side portion 250 which extends upward, and terminates at a lip 225, as illustrated in FIG. 14B. The side portion 250 and lip 225 extend along the outer circumference of the mid lens 200, thereby defining a notch 230.

Prior to insertion into the eye, the top lens 300 engages the notch 225 of the mid lens, such that a seal is formed between the notch 225 and the top lens 300, and which holds the mid lens 200 and the top lens 300 together as a single assembly (FIG. 16). The top lens 300 is oriented so that, when the top lens 300 is inserted into the mid lens 200, raised projections or notches 305 of the top lens 300 face the mid lens 200 or may also project away from the mid lens 200. The notches or projections 305 can provide directional and axial orientation for the top lens, similar to the axis orientation marks 85 of FIG. 5.

The lens manufacturer assembles the mid lens 200 and the top lens 300 to a predetermined axis orientation to correct the astigmatism, and then the surgeon, outside the eye assembles the front lens assembly 200, 300, and the base lens 100 and inserts the completed assembly into the eye as one folded piece such that the mid lens 200 is sandwiched between the base lens 100 and top lens 300. Alternatively, the surgeon inserts the top lens 300 and the mid lens 200 assembly into the eye and then attaches the assembly to the base lens 100 by sliding a projection 210 of the mid lens 200 into a slot 110 of a corresponding flange 105 of the base lens 100, the latter two step assembly allows for a smaller surgical incision. Once the first projection 210 is in place in the corresponding first slot 110, if more projections are present in the mid lens 200, then the surgeon adjusts the mid lens 200 and the top lens 300 until the other projection(s) 210 line up with the other slot(s) 105. Once all projections 210 have been inserted into their corresponding slots 110, the assembly of the top lens 300 and the mid lens 200 is secured in the base lens 100, and the procedure is completed.

In the event that the assembly formed by the mid lens 200 and the top lens 300 requires replacement, the surgeon may perform a disassembly procedure as discussed herein. First, a cannula containing visco elastic material would be introduced into the eye and positioned at the interface between the lens assembly (mid lens 200 and top lens 300) and the base lens 100. The injection of visco elastic causes the mid 200/top 300 lens assembly to elevate, thus disengaging the projections 210 from the slots 110 in the base lens 100. The original lens assembly would then be removed from the eye, and a new lens assembly placed into the eye and attached to the base lens 100 similar to as described above in the primary operation.

The inventor's application Ser. No. 12/000,364 taught a different orientation of the mid lens and top lens than the orientation disclosed in the inventor's '875 application. For example, the '364 application inverted or reversed the order of the mid lens and top lens such that the top lens is placed on top of the base lens and the mid lens then positioned on top of the top lens such that the three components are oriented in an order where the base lens is most posterior relative to the patient's eye. The top lens is then placed on the base lens and the mid lens arranged on the top lens such that the mid lens is most anterior relative to the patient's eye and the top lens is arranged between or in the middle of the base and mid lens.

Moreover, while the inventor's '875 application teaches the mid lens includes a notch with which a projection of the top lens engages to securely maintain the mid/top lens assembly, the inventor's '364 application joins the top and mid lenses to each other using a joining means, such as, for example, a medical adhesive that is applied in at least one location where the mid lens interfaces with the top lens.

Further, the inventor's '364 application teaches a feature wherein the haptic of the mid lens has projections extending anteriorly and posteriorly that capture the top lens (circular configuration) and retain the top and mid lens (circular configuration) as an optical assembly.

As shown in FIGS. 17A-21, the inventor's '364 application discloses a medical adhesive MA is used to join the mid lens 200' and top lens 300', respectively, together as a single, integrated unit or assembly. For example, FIGS. 17B and 18 illustrate how the medical adhesive MA is applied to the inner surface 250a of a side portion 250' of the mid lens 200' and/or an outer peripheral surface 350a of the top lens 300' to securely retain the mid lens 200' and top lens 300' together. Alternatively, as shown in FIGS. 19-21, the inventor's '364 application teaches that the medical adhesive MA can also be applied along an upper surface of the mid lens 200" and/or an entire lower surface of the top lens 300", either entirely or in select, discrete locations thereon, which directly opposes the upper surface of the mid lens 200" to join the top and mid lenses 300" and 200" into a single unit or assembly.

The inventor's application Ser. No. 12/499,613 taught manufacturing the mid lens and the top lens from a material having adhesive properties such that the mid lens and the top lens naturally adhere to each other without the need for a medical adhesive or any other joining means being administered to either of the lenses.

A certain distinguishing aspect of the '613 disclosure relative to the disclosure of the '875 and '364 applications is the material from which the top lens 3000 and the mid lens 2000 are manufactured. In the '613 application, the mid lens 2000 and top lens 3000 are manufactured from a preferably foldable material, e.g., hydrophilic acrylic, hydrophobic acrylic, silicone and the like, such that the mid and top lenses 2000 and 3000 inherently or naturally adhere or stick to each other such that the adhesive MA of the '364 application is not necessary, as is seen with hydrophilic acrylics. That is, as shown in FIG. 22, the top lens 3000 and mid lens 2000 adhere to each other without any of the adhesive MA from the '364 application disposed between opposing faces of the lenses 2000 and 3000, or between an outer peripheral surface 3500a of the top lens 3000 and an inner peripheral surface 2500a of a side portion 2500 of the mid lens 2000, as shown in FIG. 23. As such, the adhesive MA from the '364 application is omitted from the '613 application, wherein assembly of the optical assembly including the top lens 3000 and mid lens 2000 is simplified, faster, needs less materials, and reduces the overall costs.

As shown in FIG. 24, the optical assembly, i.e., the top lens 3000 and mid lens 2000, of the '613 application, is first assembled by the lenses 2000 and 3000 being adhered together by the manufacturer. Then, at least one, and preferably two, projections 2100 of the mid lens 2000 portion of the optical assembly are passed through a corresponding slot 1100 defined in a corresponding flange 1005 of the base lens 1000 and overlaps a portion of the corresponding haptic 1200 of the base lens 1000.

FIG. 25 is a schematic diagram of a portion of the mid lens 2000 of the '613 application, which engages the top lens 3000 and also passes through or otherwise contacts the base lens 1000. The top lens 3000 is illustrated in dashed lines as abutting against the inner surface 2500a of an upper side portion 2500 of the mid lens 2000. It is possible for portions of the base lens 1000 to contact an outer surface 2500b of the side portion 2500, an upper surface 2500c of the side portion 2500, an upper surface 2100a of the projection 2100, a lower surface 2100b of the projection, and an outer surface 2100c of the projection 2100. The possible contact surfaces 2500b, 2500c, 2100a, 2100b, and 2100c are subjected to a treatment that prevents such surfaces from being able to adhere to a corresponding portion of the base lens 1000 contacted by the surfaces.

The '613 application further discloses at least one of the surfaces 2500b, 2500c, 2100a, 2100b, and 2100c can be frosted or otherwise chemically treated, or physically worked so as not to have any adhesive properties. As shown in FIG. 26a, the upper surface 2100a of the projection 2100 is frosted F with a suitable chemical or substance that prevents the mid lens 2000 from being able to adhere to the base lens 1000. Alternatively, as shown in FIG. 26b, the upper surface 2100a of the projection 2100 is roughened or knurled to have a knurled surface K.

FIGS. 27A-D illustrate another aspect disclosed in the '613 application, which shows that the optical assembly may include additional optical elements wherein the top lens 3000, mid lens 2000, and any additional lens 4000 would be provided in a stacked arrangement within the optical assembly. Any number of additional lenses may be included such that there are four, five, six, . . . twelve lenses provided in a stacked arrangement within the optical assembly. Furthermore, the order in which the lenses 2000, 3000 and 4000 are arranged in the optical assembly may be adjusted or altered. As shown in FIG. 27B, the top lens 3000 and mid lens 2000 may be switched such that the additional lens 4000 is provided between the base lens 1000 and the top lens 3000. Furthermore, as shown in FIG. 27C, the additional lens 4000 can be positioned furthest from the base lens 1000.

The '613 application further discloses that a space to be located between lenses. Referring to FIG. 27D, any one of the reference numbers, e.g., 4000, 5000, 6000 and 7000, could represent or illustrate a space or gap between neighboring lenses. Also, a chamber to be defined between neighboring lenses, wherein the chamber would hold or contain a liquid, or semi-solid, or a gelatinous material having pharmacological and/or optical properties.

In another embodiment of the '613 application, illustrated in FIG. 28, the mid lens 2000 and top lens 3000 are combined to form an integrated, single lens 8000 that engages the base lens 1000 to form the optical assembly. For example, as described in the '613 application, a bottom surface of the lens 8000, that is, the half of the lens 8000b closest to the base lens 1000, can be or define a non-toric surface, while a top surface of the lens 8000a furthest from the base lens 1000, can be or define a toric surface. The optical properties of the sections of the lens 8000a and 8000b can be formed by lathing or molding the surfaces to produce the toric, non-toric, multifocal, etc. optical properties. The surgeon further customizes the lens 8000 by its surgical orientation in the eye, which is determined by the surgeon at the time of the primary surgery. Alternatively, the surgeon can use a fully customized front lens assembly 2000, 3000, 4000, 5000, 6000, 7000, where the orientation is set by the manufacturer as specified by the surgeon (fully customized manufacturing).

However, there remains a need in the art for an intraocular lens assembly that provides a simpler design, an alternative method of orienting lenses, a method of delivering pharmacological compounds, a design that allows for smaller incisions and components that are easier to replace.

SUMMARY OF THE INVENTION

It is an aspect of this invention to provide a multi-component intraocular lens system with components that are removable and replaceable after placement in the eye.

It is an additional aspect of the present invention to provide a multi-component intraocular lens system with a single front lens milled to form tabs that establish an orientation of the single front lens. The tabs establish the orientation without the need for a two-lens optical assembly.

It is a further aspect of this invention to provide a method of implanting a multi-component intraocular lens system, the method including a step of fusing a flange to a base lens and a step of engaging an optical assembly or front lens with the base lens via an aperture defined within the flange.

Further, the present invention includes a feature wherein non-optical portions of the intraocular lens system are manufactured of a material that is capable of releasing a pharmacological agent. For example, at least one haptic of the base lens may be manufactured of the material that is capable of releasing a pharmacological agent to the eye.

Moreover, to allow for a smaller incision, the corrective power needed to correct the vision of a patient may be divided between additional lenses of the optical assembly and the base lens. Additionally, if only a single front lens is engaged with the base lens, the power may be divided between the front lens and the base lens. By reducing the power of the base lens, the base lens is smaller, thereby requiring a smaller incision for implantation of the intraocular lens system.

Further, the present invention includes a feature wherein the base lens has a diameter different from the diameter of the front lens or optical assembly. As such, the capsule of the eye is more likely to "cellophane wrap" the base lens and less likely to "cellophane wrap" the front lens or optical assembly. For example, the front lens or optical assembly may have a larger diameter than the base lens. Furthermore, the front lens or optical assembly may have rounded edges and the base lens may have sharp edges to encourage cellophane wrapping of the base lens and discourage cellophane wrapping of the front lens or optical assembly.

Additionally, aspects of the present invention provide for a base lens for delivering pharmacological agents without including an optical portion. An aspect of the present invention also provides an apparatus and method for replenishing a level of pharmacological agents within a base lens In an aspect of the present invention an intraocular lens assembly has a series of orientation holes that serves the dual function of providing a relative orientation of the lenses as well as providing an access path to a base lens.

In another aspect, a base lens has a simpler and easier to manufacture structure while maintaining flanges for engaging a front lens assembly.

BRIEF DESCRIPTION OF THE FIGURES

In the drawings:

FIGS. 4A-4B are top and side views, respectively, of a type of compound intraocular lens-top lens component;

FIGS. 5A-5B are top and side views, respectively, of a type of compound intraocular lens-top lens component;

FIG. 12A is a top view of a base component of a currently known foldable multi-component intraocular lens;

FIG. 12B is a side view of an enlarged portion of the base component shown in FIG. 12A;

FIGS. 14A and 14B are an exploded top view and an exploded side view, respectively, of a mid lens replaceable component of a currently known foldable multi-component intraocular lens;

DETAILED DESCRIPTION OF THE PREFERRED EMBODIMENTS

Figure 29A:
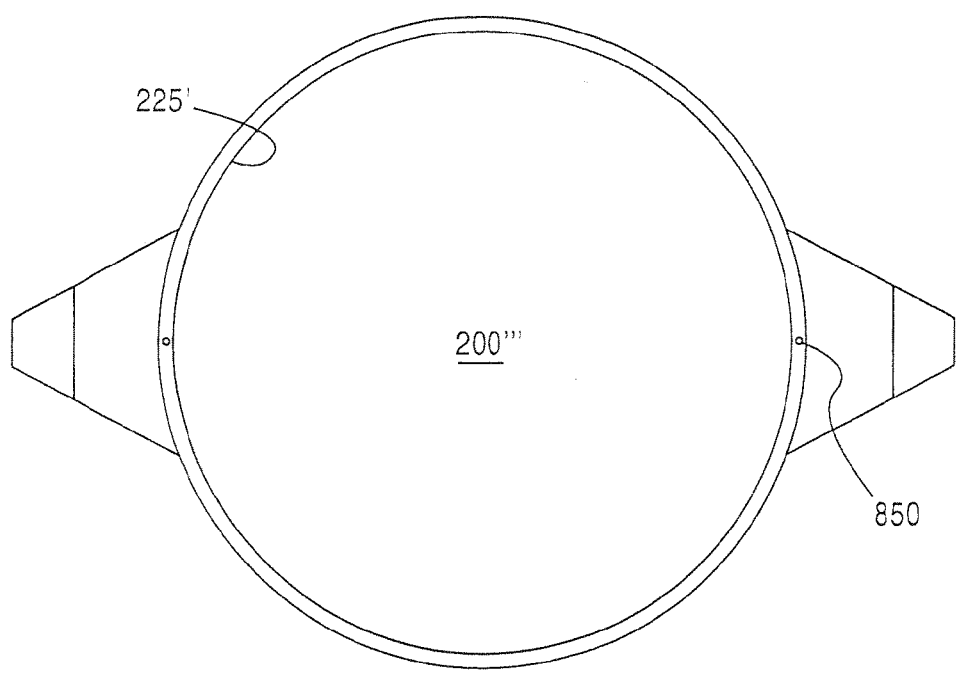
FIG. 29a is a top view of an assembly having an orientation hole according to one aspect of the present invention.
Figure 29B:
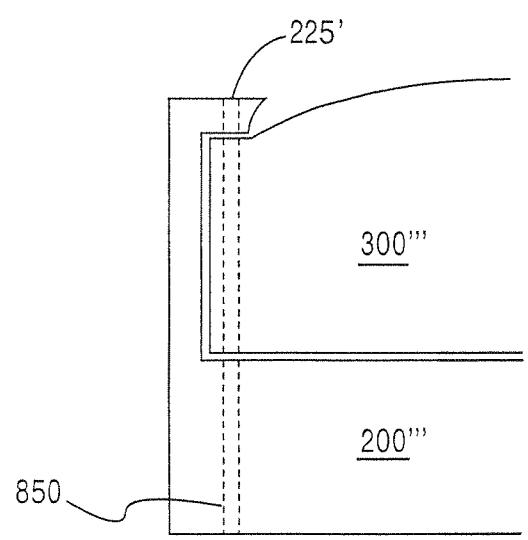
FIG. 29b is a side view of the assembly of FIG. 29a, wherein a top lens is inserted into the mid lens.

As discussed above, and shown in FIG. 5A, in the applicant's prior intraocular lens assembly, axis orientation marks may be provided to aid in positioning and orienting a top lens of a MC-IOL. In an aspect of the present invention, instead of providing axis orientation marks, the MC-IOL is provided with an access bore 850. As shown in FIG. 29a, the access bore 850 may be provided at opposing points along the collar 225' to indicate an axial orientation. The axial orientation indication of the access hole 850 serves essentially the same function as the orientation marking described above. However, as shown in FIG. 29b, unlike the orientation marking, the access bore 850 extends from the collar 225" through an outer radial portion of a top lens 300" and a mid lens 200", and through a lower portion of the top lens 300" and mid lens". Accordingly, the access bore 850 serves an additional function of providing an access path to an abutting region defined between the mid lens 200''' and a base lens (not shown). In an aspect of the present invention the access bore 850 is sized to accommodate a needle that may be used as part of a surgical procedure.

Figure 1:
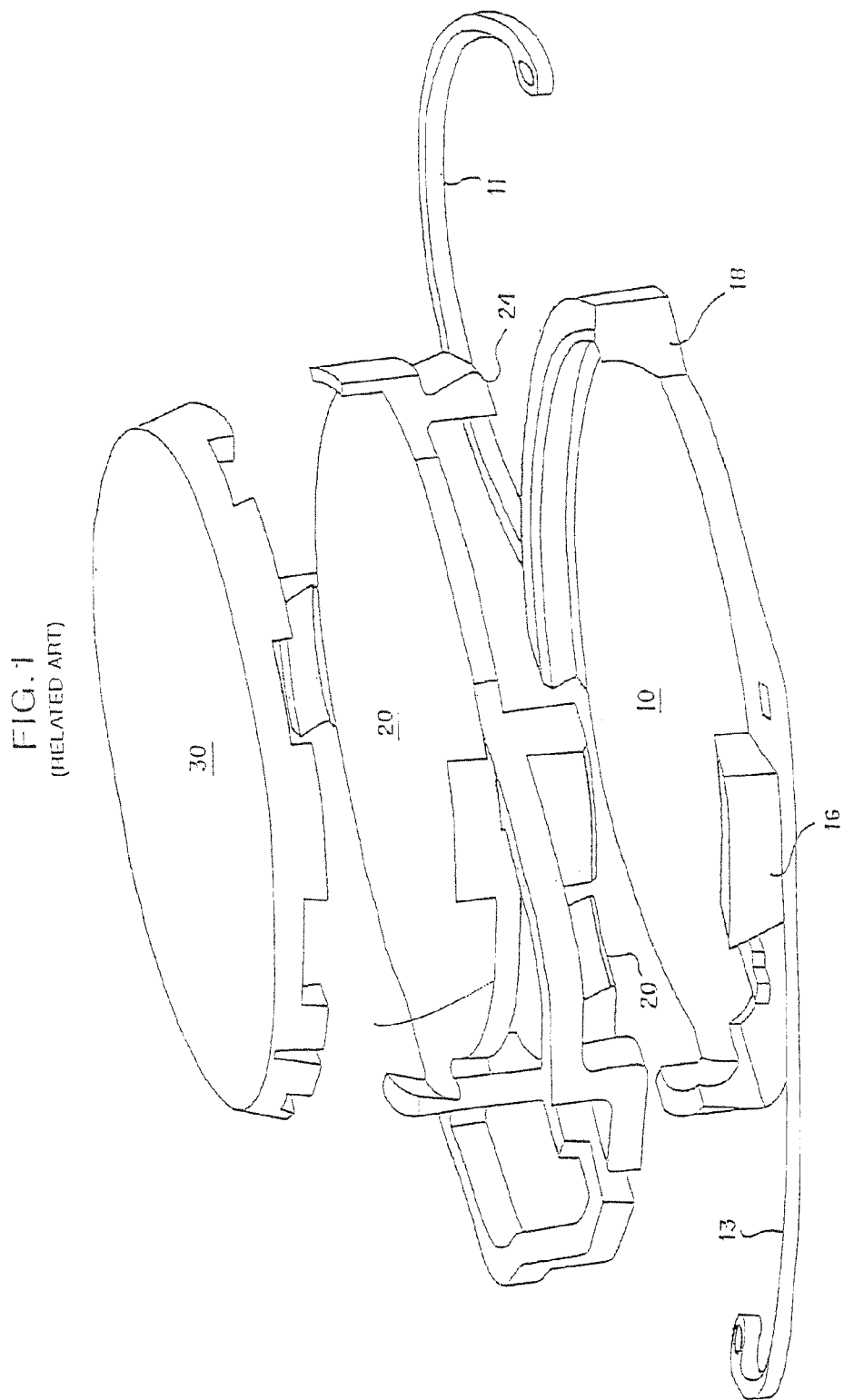
FIG. 1 is a plan view of the base, mid, and top lens components of a currently known multi-component intraocular rigid lens.
Figure 2:
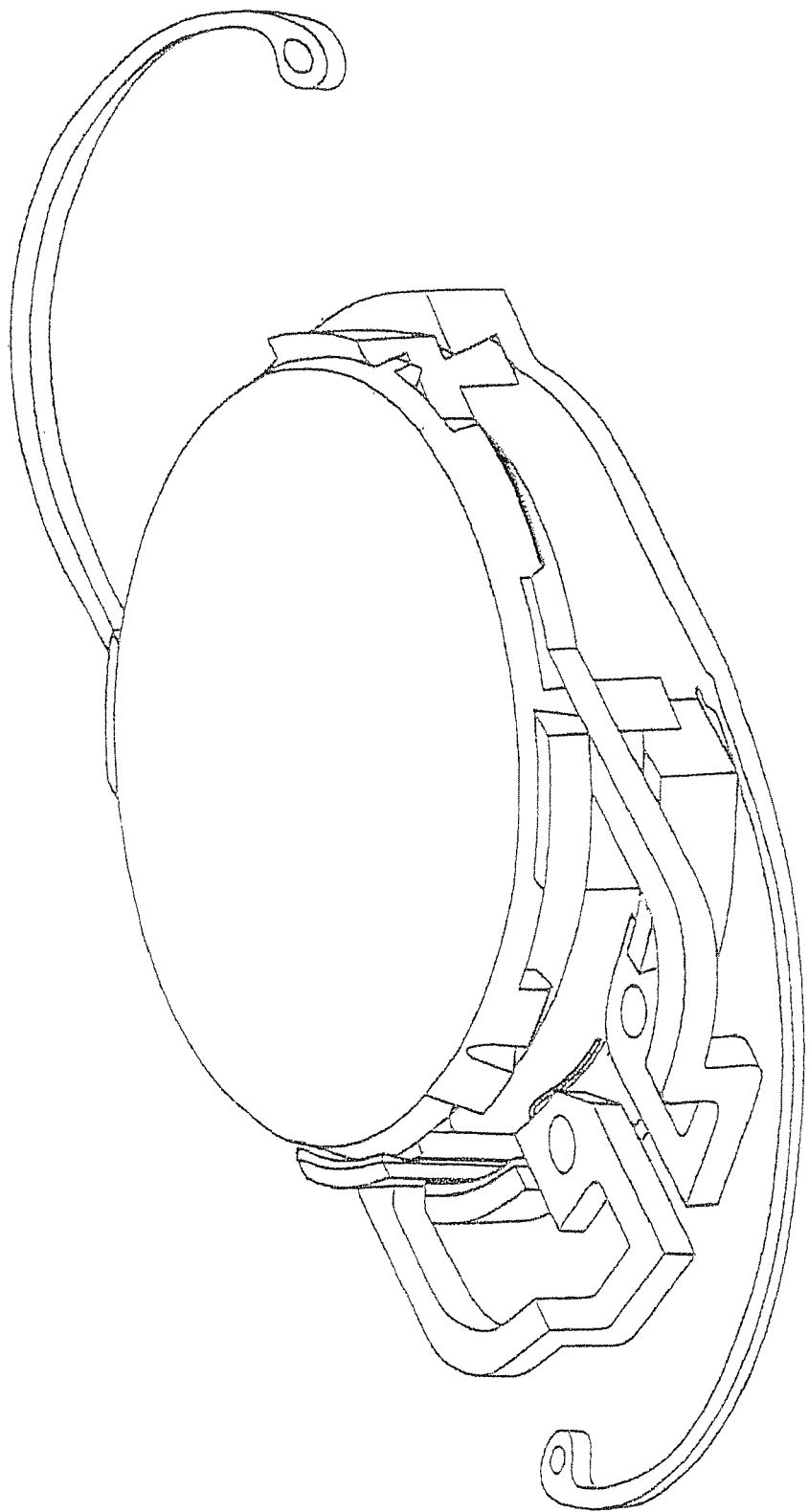
FIG. 2 is an exploded side view of the assembled base, top, and mid lenses of the currently known multi-component intraocular rigid lens shown in FIG. 1.
Figure 3A:
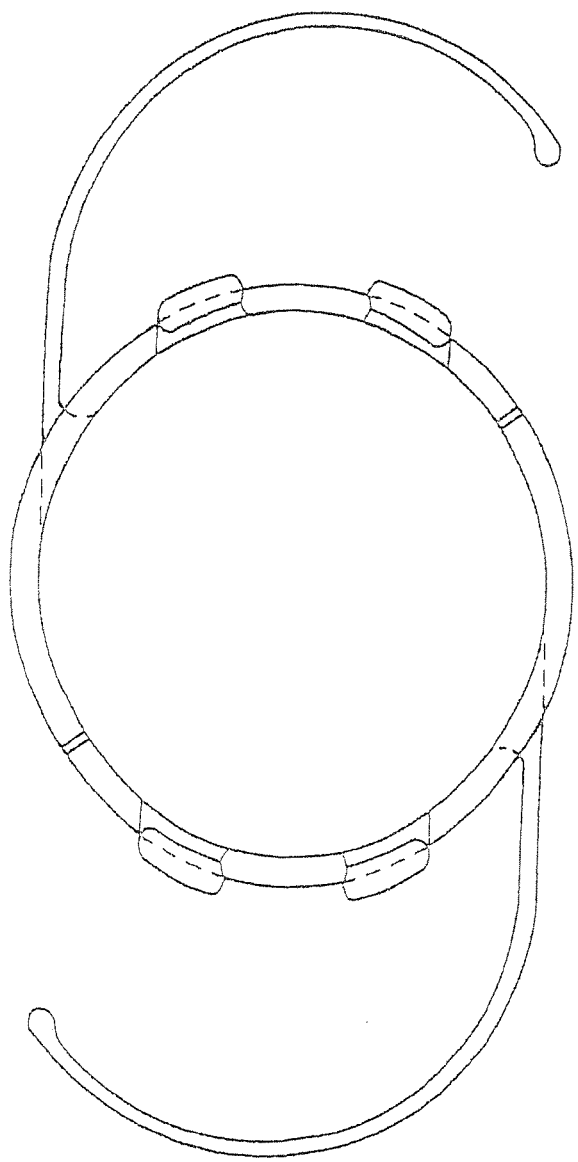
FIGS. 3A-3B are exploded views of a currently known two component compound intraocular lens.
Figure 3B:
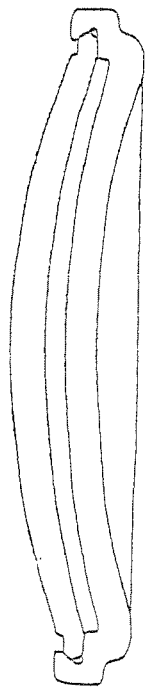
Figure 6:
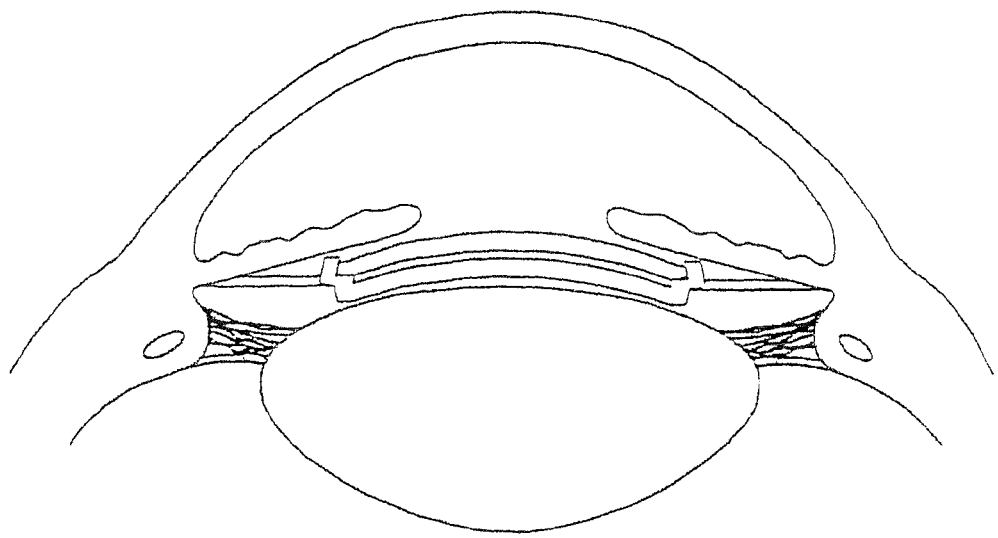
FIG. 6 is a side view of a compound intraocular lens implanted within a human eye ciliary sulcus.
Figure 7:
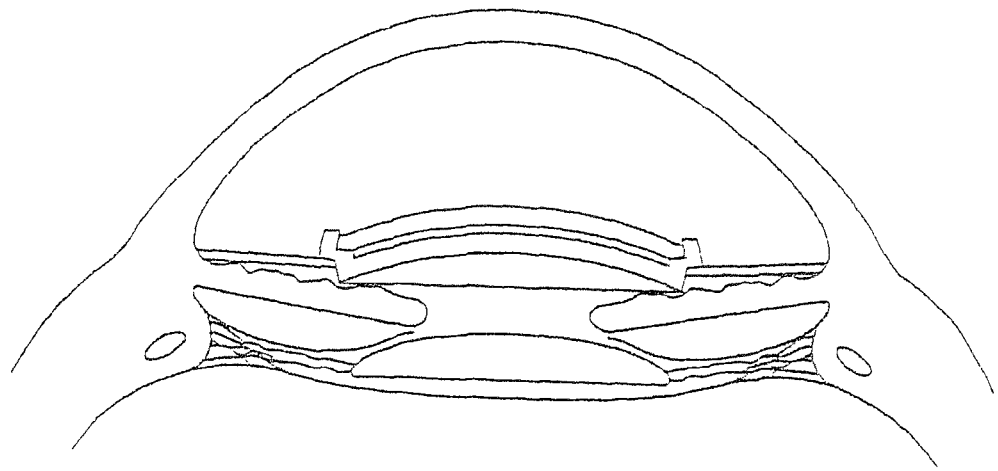
FIG. 7 is a side view of another compound intraocular lens implanted within a human eye using the anterior chamber angle as support.
Figure 8:
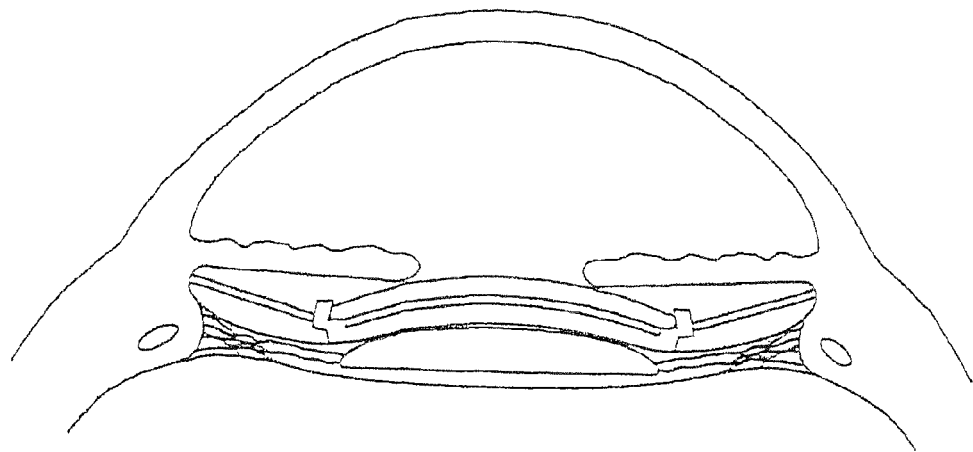
FIG. 8 is a side view of a sulcus mounted compound intraocular lens implanted within a human eye with a previously implanted single component conventional intraocular lens mounted in the capsular bag.
Figure 9:
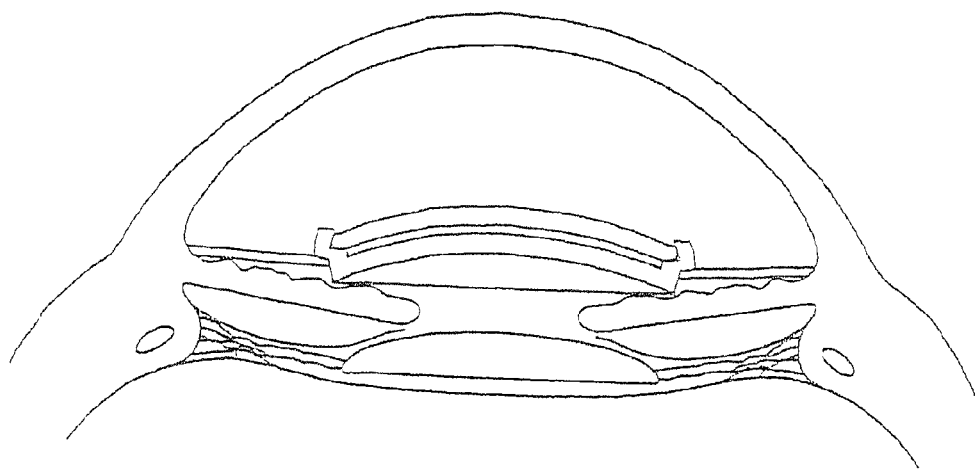
FIG. 9 is a side view of an anterior chamber mounted compound intraocular lens implanted within a human eye with a previously implanted single component conventional intraocular lens mounted in the capsular bag.
Figure 10:
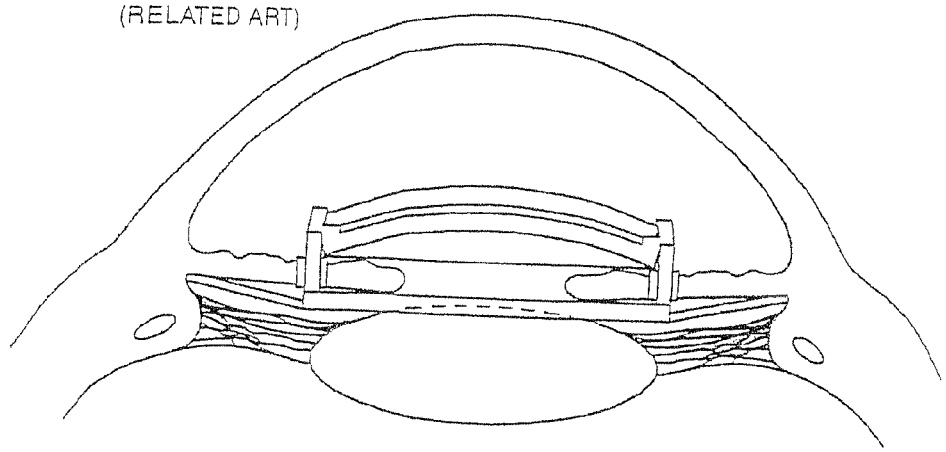
FIG. 10 is a side view of an anterior chamber mounted compound intraocular lens on a support secured in the posterior chamber and is implanted within a human eye with a previously implanted single component conventional intraocular lens mounted in the capsular bag.
Figure 11:
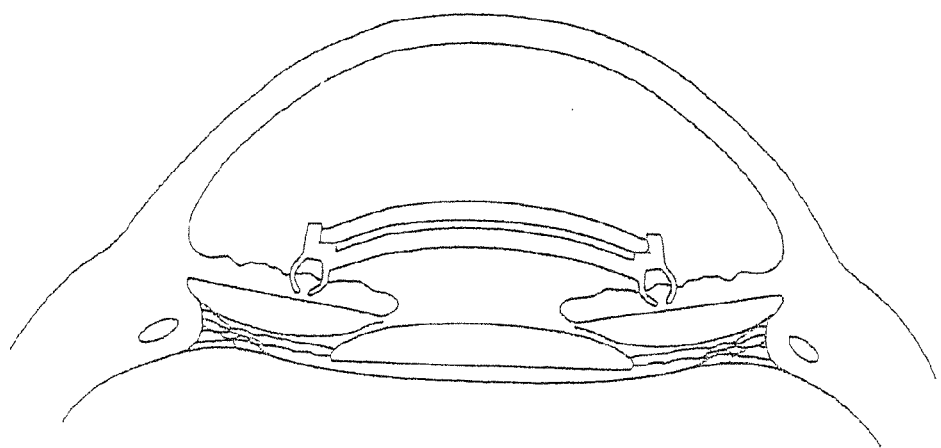
FIG. 11 is a side view of an iris fixated compound intraocular lens in the anterior chamber that is implanted within a human eye with a previously implanted single component conventional intraocular lens mounted in the capsular bag.
Figure 13:
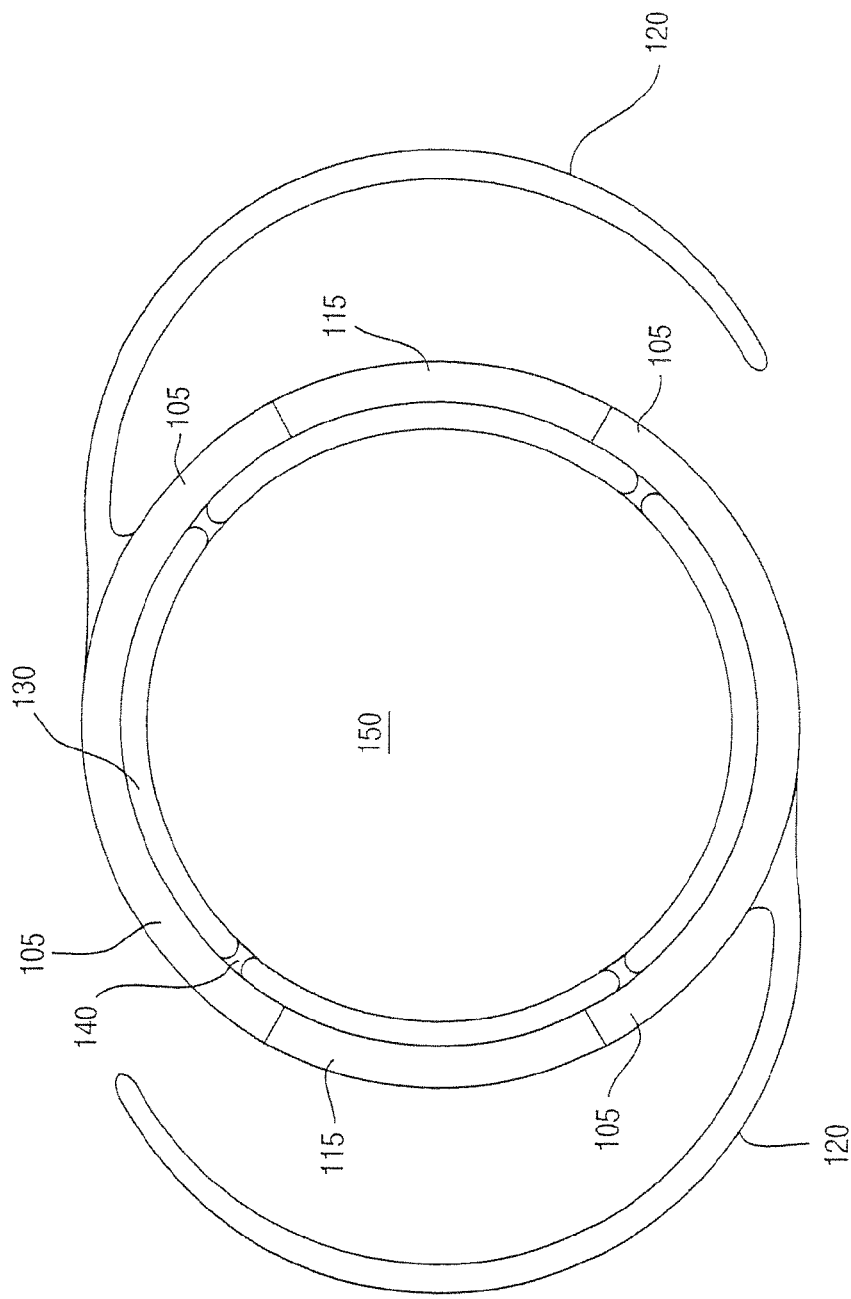
FIG. 13 is a top view of a base component of another currently known foldable multi-component intraocular lens.
Figure 15:
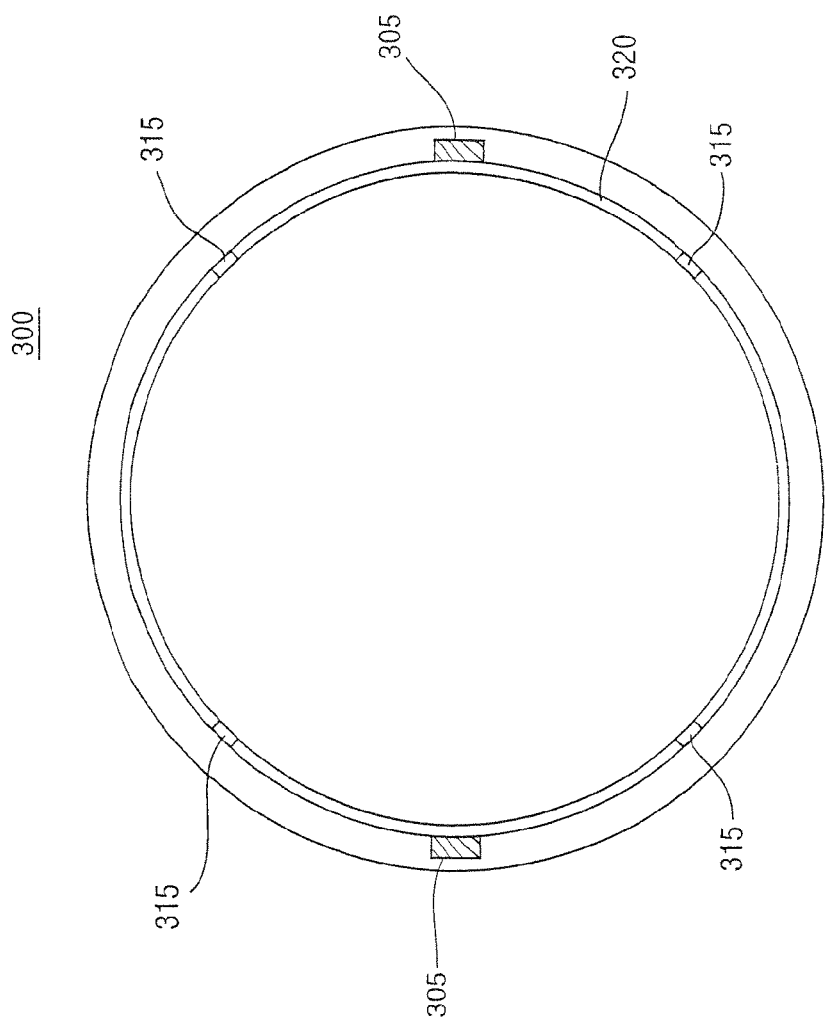
FIG. 15 is an exploded top view of the top lens component of a currently known foldable multi-component intraocular lens.
Figure 16:
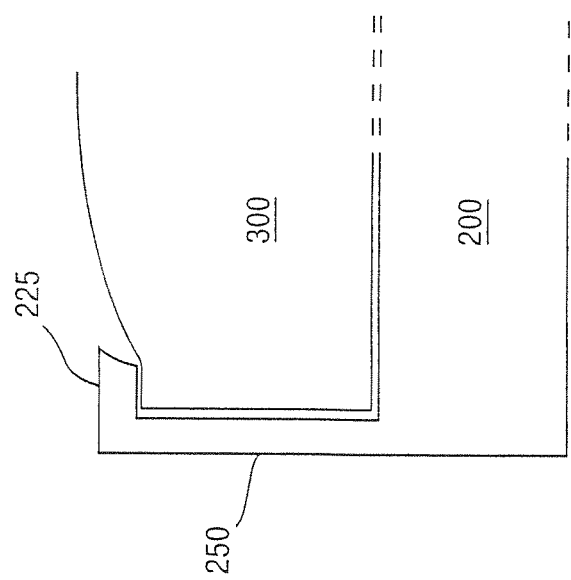
FIG. 16 is a side view of a currently known optical assembly wherein a top lens is inserted into a mid lens.
Figure 17B:
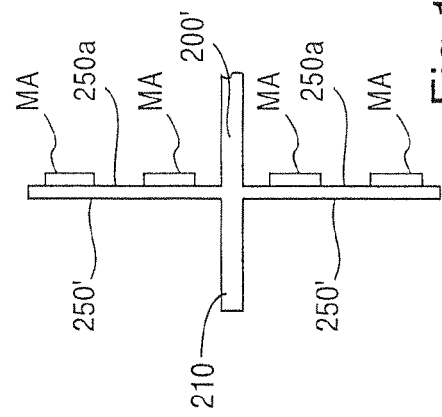
FIGS. 17A and 17B are a top view and an exploded side view, respectively, of a top lens replaceable component of a currently known foldable multi-component intraocular lens.
Figure 17A:
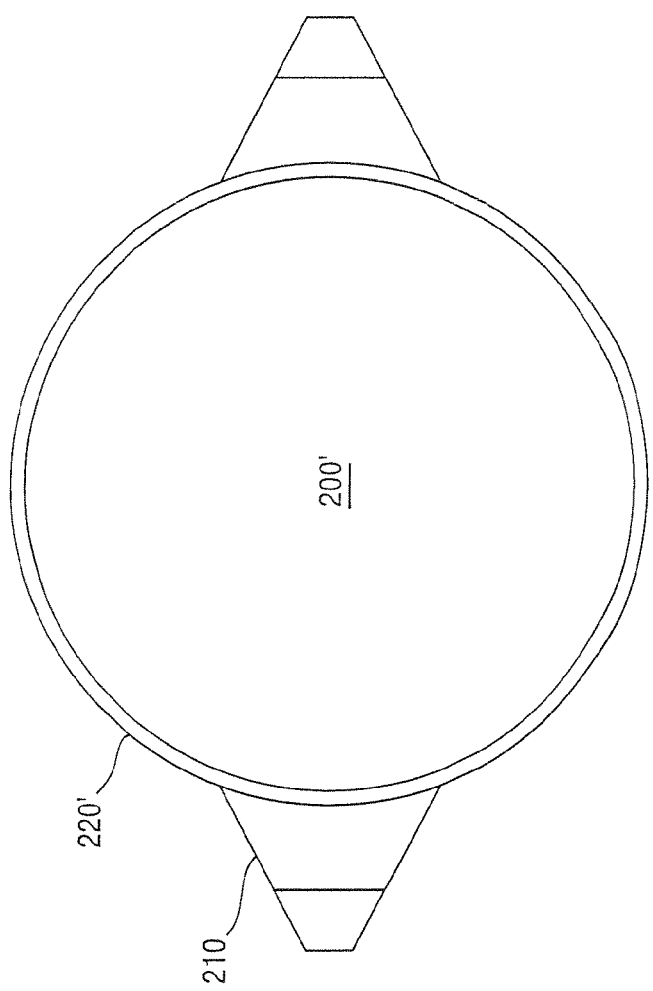
Figure 18:
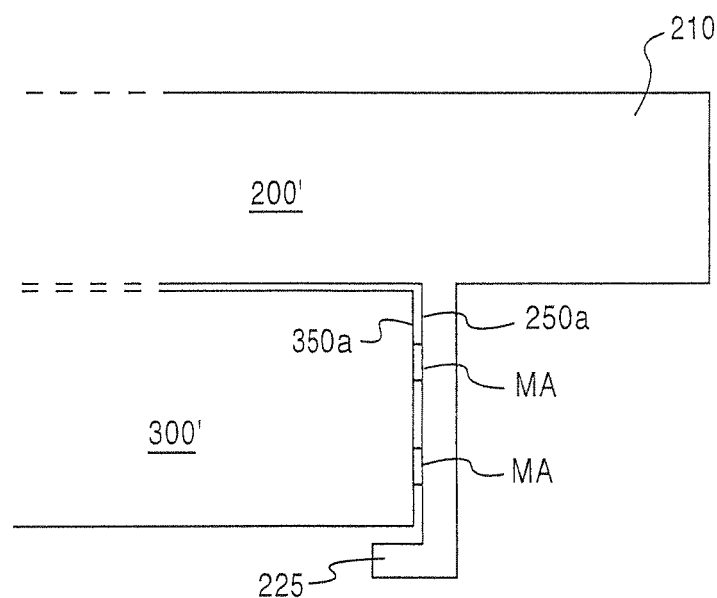
FIG. 18 is a side view of a currently known optical assembly wherein a mid lens engages a top lens.
Figure 19:
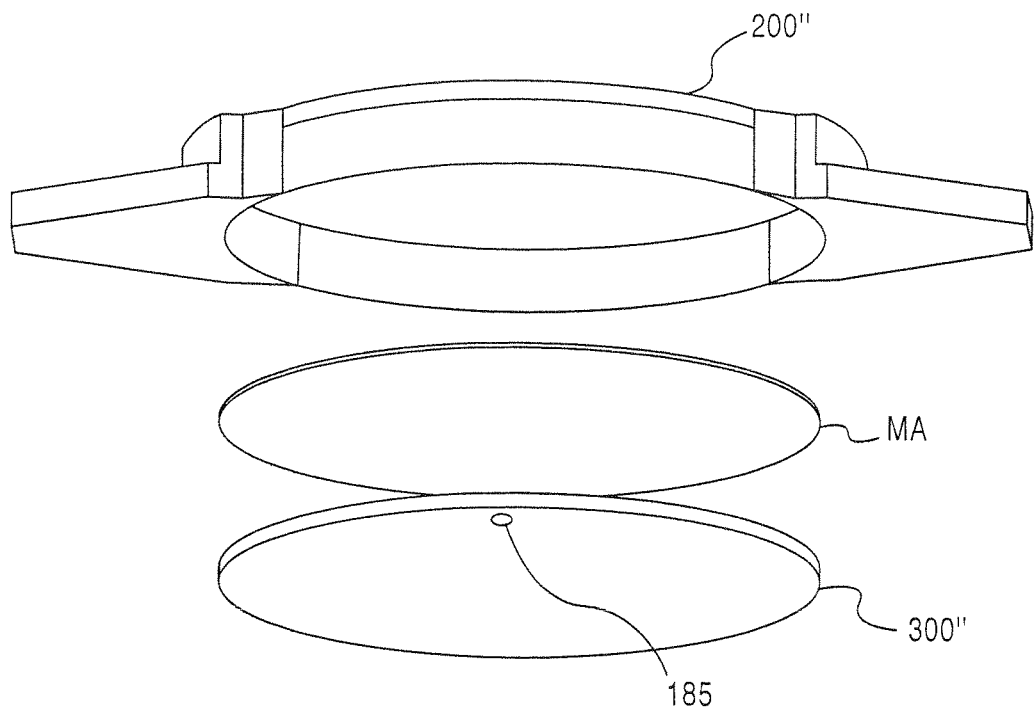
FIG. 19 is an exploded view of a currently known optical assembly.
Figure 20:
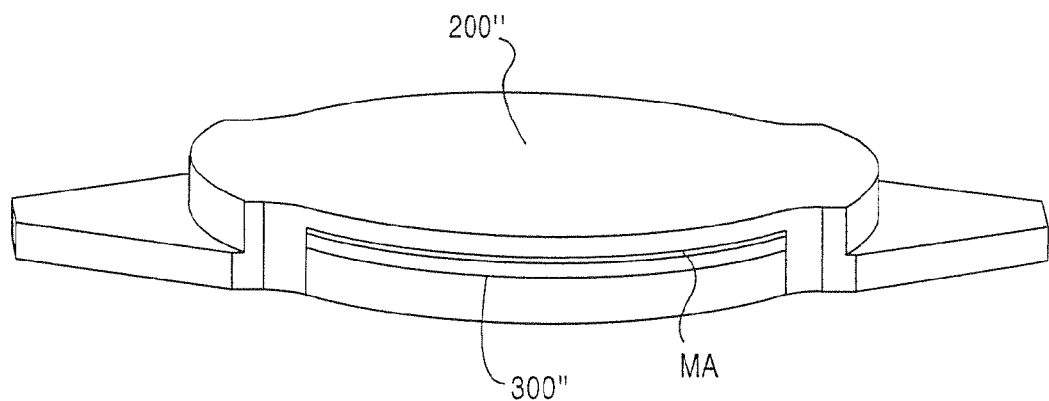
FIG. 20 is a perspective view of the optical assembly shown in FIG. 19 in the assembled state.
Figure 21:
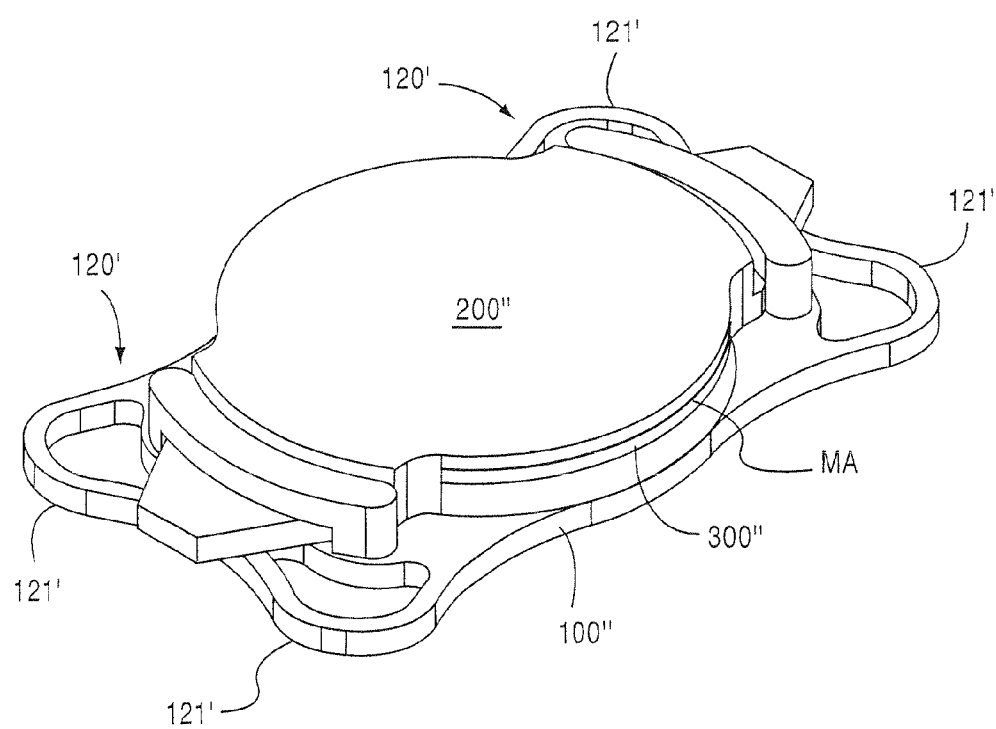
FIG. 21 is a perspective view of the optical assembly shown in FIG. 20 assembled with a base lens.
Figure 22:
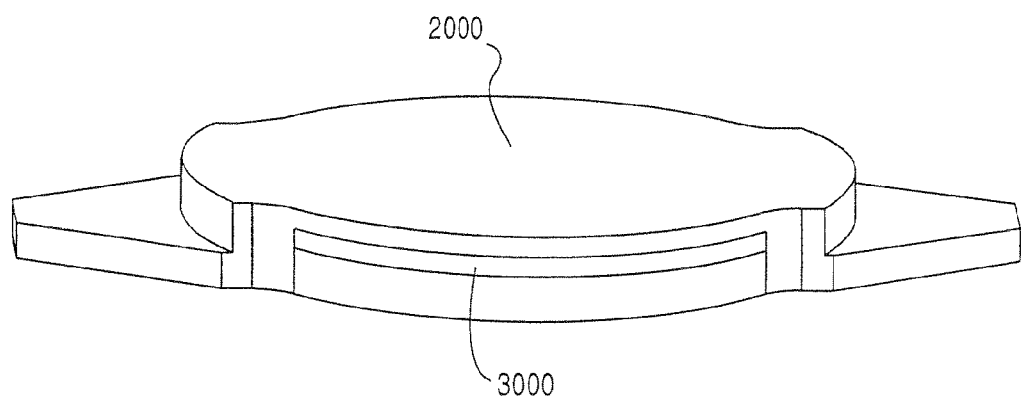
FIG. 22 is a perspective view of a currently known optical assembly wherein a top lens and a mid lens are adhered to each other without the use of an adhesive provided therebetween according to an embodiment of the present invention.
Figure 23:
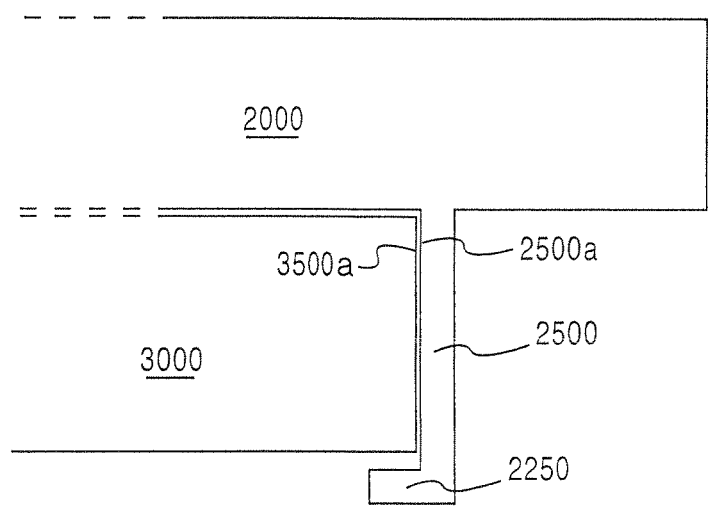
FIG. 23 is a side view of the optical assembly shown in FIG. 22, illustrating a region where the mid lens engages the top lens.
Figure 24:
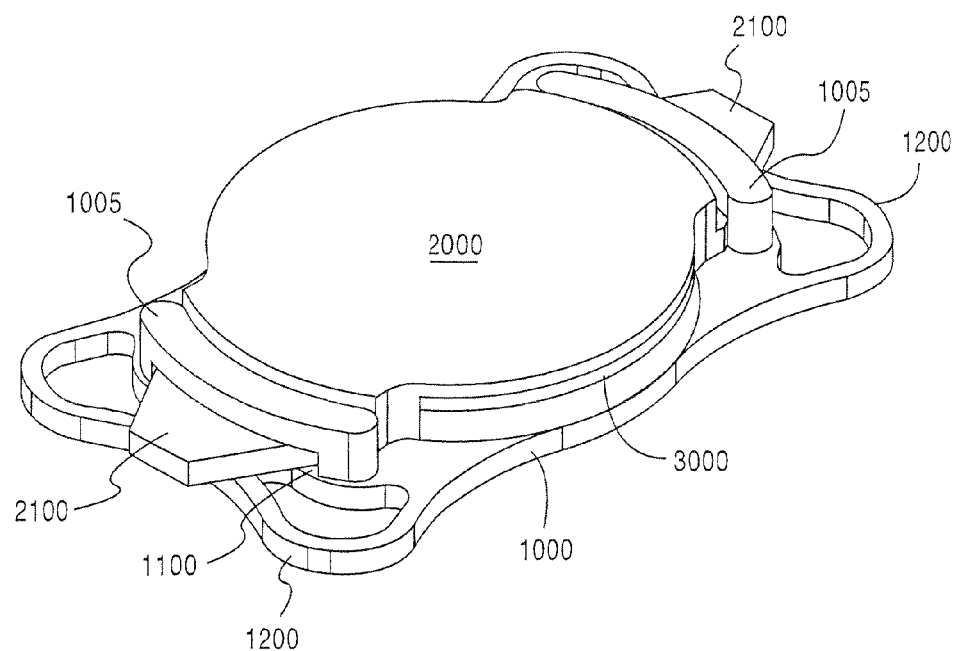
FIG. 24 is a perspective view of the optical assembly shown in FIG. 22 assembled with a base lens.
Figure 25:
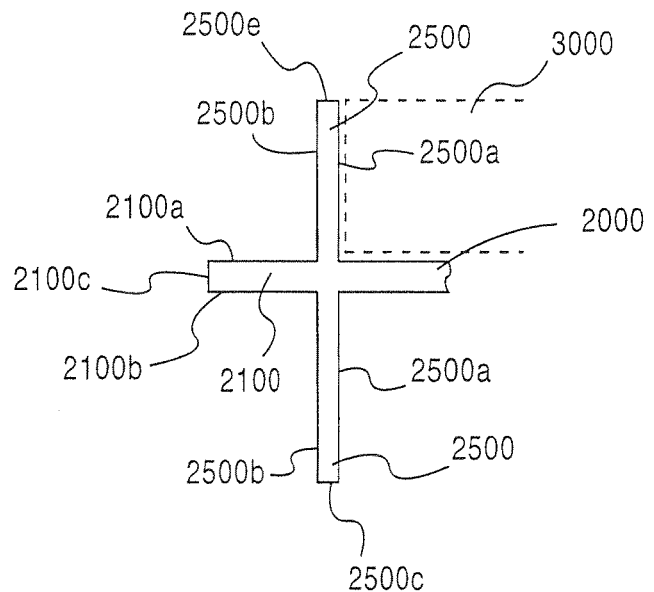
FIG. 25 is an exploded side view of a currently known top lens illustrating regions that can be treated to have non-adhesive properties.
Figure 26A:
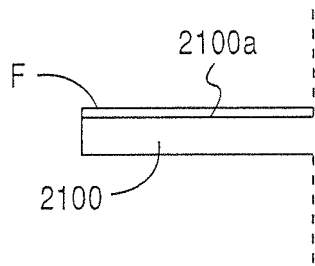
FIGS. 26A and 26B are schematic diagrams illustrating examples of how the regions illustrated in FIG. 25 can be treated.
Figure 26B:
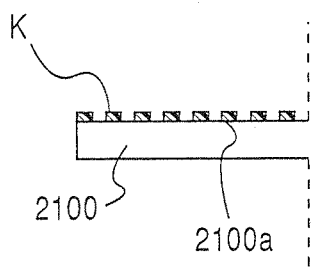
Figures 27A, 27B, 27C, 27D, 28:
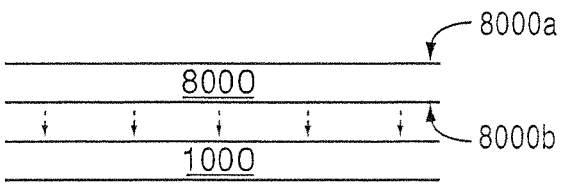
FIGS. 27A-27D are schematic diagrams that illustrate various currently known manners in which the lenses of the optical assembly can be arranged.
FIG. 28 is a schematic diagram of a currently known embodiment wherein the mid lens and top lens are integrated into a single lens that is placed within the base lens.

As discussed above, and shown in FIGS. 14-15, in the applicant's prior intraocular lens assembly, the mid lens 200 may allow for spherical or multifocal adjustments, while the top lens carries the astigmatic correction. Either, the lens manufacturer assembles the mid lens 200 and the top lens 300 to a predetermined axis orientation to correct the astigmatism (enhancement surgery), or the surgeon orients the assembled front lens assembly 200, 300 inside the eye once it is attached to the base lens (primary surgery).

Figure 30A:
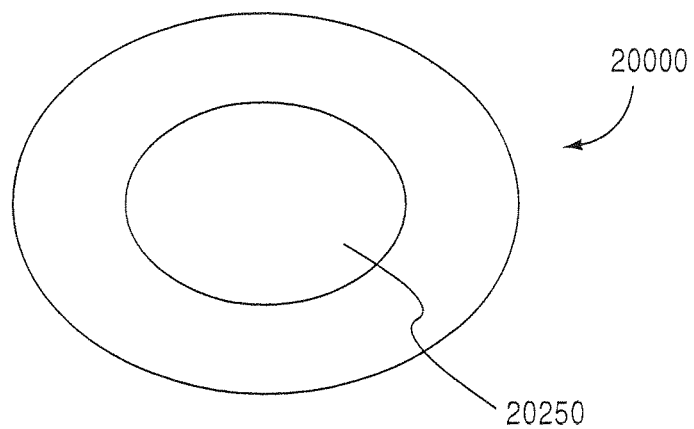
FIG. 30a is a top view of an unmilled front lens according to one aspect of the present invention.

However, as discussed above, there are instances where the mid lens and top lens are combined in an integrated, single lens that engages the base lens. As described above, a bottom surface portion of the single lens can be or define a non-toric or spherical and/or multifocal surface, while a top surface portion of the single lens can be or define a toric or non-spherical, and/or multifocal surface, and/or spherical. It is also within the scope of the invention that the optical properties of the surfaces may be reversed, e.g., the bottom surface is toric and the top surface is non-toric. FIG. 30*a* shows an aspect of the present invention, wherein a single front lens 20000 includes a top lens portion 20250 and a bottom lens portion opposing the top lens portion. In the single front lens 20000 of the present invention, the top lens portion 20250 and the bottom lens portion 20200 are two portions of a single lens. Because the portions are fixed relative to each other, an axial orientation can be established by rotating the entire lens assembly or by the manufacturer milling tabs 20100 to a predetermined orientation.

Figure 30B:
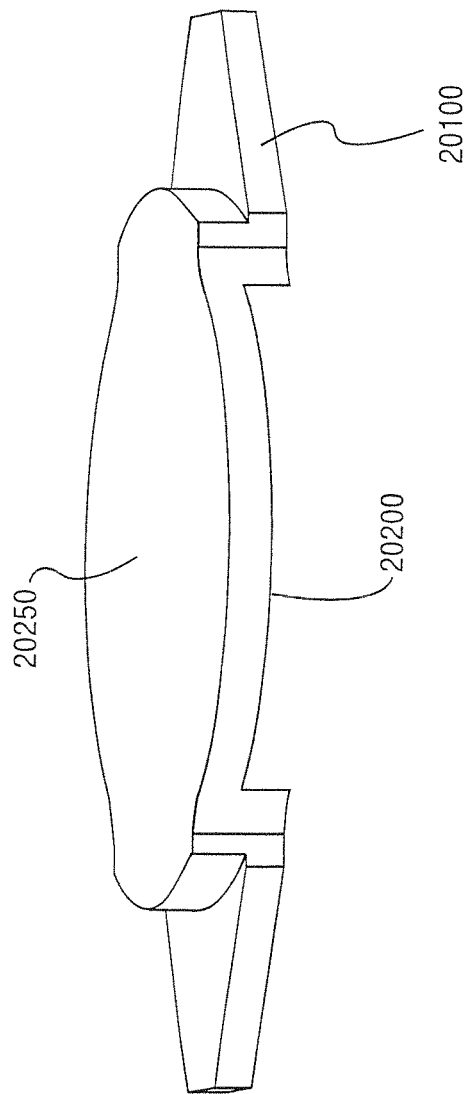
FIG. 30b is a side view of the front lens of FIG. 30a after milling according to one aspect of the present invention.

Unlike the lens assembly described in the '875 application, in the present invention, when the top and bottom lens portions are fixed relative to each other, the orientation of the single front lens 20000 may be established by the manufacturer, according to the specifications of the surgeon. Before the manufacturer establishes the orientation, the front lens 20000 begins as a circular lens, having a top lens portion 20250, as shown in FIG. 30*a*, and a bottom lens portion opposing the top lens portion 20250. As shown in FIG. 30*b*, the manufacturer then cuts or mills the front lens 20000 to remove a portion of the lens material, thereby creating flanges or tabs 20100 positioned at particular locations corresponding to a predetermined axial orientation of the front lens 20000. The tabs 20100 extend radially outward from the front lens 20000. As shown in FIG. 30*b*, when formed in this manner, the tabs 20100 may extend substantially below the milled bottom portion 20200 to allow the single front lens to mate with a base portion or to allow additional lenses to be inserted in between the single front lens and the base lens. Accordingly, by cutting or milling the single front lens 20000, the orientation for treating a patient with astigmatism can be established at the manufacturing stage. The completely manufactured front lens 20000 may then be implanted in the manner described above.

In another aspect of the present invention, any of the intraocular lens assemblies described above may further include pharmacological agents useful for treating conditions of the eye. Pharmacological agents may be infused in any part of the intraocular lens assembly that would not interfere with the optics portion. For example, the pharmacological agents may be any one of: anti-cancer agents, antibiotics, steroids, glaucoma medicine, non-steroidal anti-inflammatory agents, agents for treating macular edema such as ranibizumab (trade name Lucentis) or bevacizumab (trade name Avastin), among others. Particular materials must be used that are capable of storing and releasing pharmacological agents, while also being inserted in the human eye. For example, a clear plastic material that slowly releases the agent is suitable. Additionally, the materials and pharmacological agents may be chosen based on the particular condition being treated. For example, it may be desirable for the pharmacological agent to be released after a predetermined period of time has lapsed after the surgery, to be released at a predetermined rate, or to be released periodically. Furthermore, the material may be chosen to allow replenishing of the delivery system. It is also within the scope of the invention that the materials and the pharmacological agents are chosen such that the pharmacological agents are released during particular environmental conditions. For example, during night or day, when the eye is dry or moist, when the eye is closed or open, when the eye is irritated, etc. Because these materials are generally opaque, the optical portions of the lenses, which must be transparent relative to the remaining portions of the lenses, are generally not manufactured from a material that is capable of storing and releasing pharmacological agents. Therefore, in a preferred embodiment, only the remaining, non-optical portions are made of the material. For example, the haptics (13, 120, 210, 1200), the flanges (105, 1005), and/or the projections (2100) of the above-described intraocular lens assemblies may be made of the material capable of storing and releasing pharmacological agents. It is within the scope of the invention, however, that any non-optical portion of any of the above-described intraocular lens assemblies may be composed of the material capable of storing and releasing pharmacological agents.

Similarly, in another aspect, the non-optical portions of a front lens may be opaque to aid in positioning or manipulating the front lens relative to the base lens. For example, the tabs 20100 shown in FIG. 30*b*, may be opaque. As with the base lens discussed above, the optical portion of the front lens is transparent. However, when the entire front lens is transparent it may be difficult for a surgeon to locate the particular part of the front lens to be manipulated or to ensure the lens is properly positioned. By using the opaque portions as a guide, the surgeon will be able to more easily manipulate and position the front lens.

Figure 31:
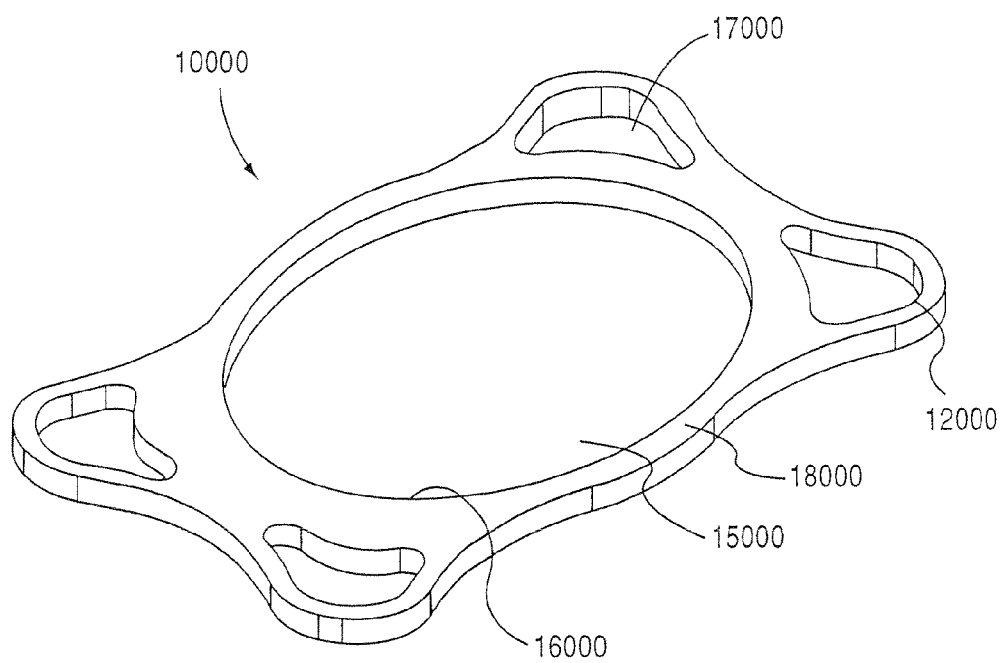
FIG. 31 is a perspective view of a base lens according to one aspect of the present invention.

In another aspect of the present invention, as shown in FIG. 31, a pharmacological dispensing apparatus 10000 dispenses pharmacological agents, wherein the dispensing apparatus does not have an optical portion. In this aspect, the pharmacological dispensing apparatus 10000 is similar to the base lens described above, the difference being that while the pharmacological dispensing apparatus 10000 has similar haptics 12000 to the base lens described above, there is an aperture 15000 where the optical portion would be. As illustrated in FIG. 31, in an exemplary aspect, the haptics 12000 on opposing ends of the base lens 10000 are connected by a connecting member 18000. The aperture 15000 is defined by an inner periphery 16000 of the connecting members 18000, and has substantially the same shape as the optical portion described above. Furthermore, the base lens 10000 may comprise additional apertures 17000 defined in each of the haptics 12000. By not having an optical portion, the pharmacological dispensing apparatus may be solely dedicated to dispensing pharmacological agents without interfering with the optics of the eye. Accordingly, the pharmacological dispensing apparatus 10000 of the eye may be useful for patients that do not need to correct their vision, but have other eye conditions that require pharmacological treatment. The pharmacological dispensing apparatus may be formed of the same material and comprise the same pharmacological agents listed above.

Figure 32A:
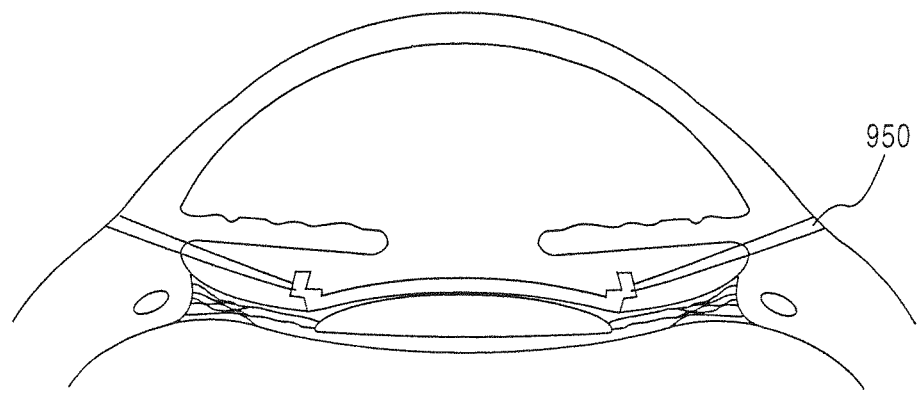
FIG. 32a is a side view of an intraocular lens implanted within a human eye ciliary sulcus, wherein a base lens includes a communicating element.
Figure 32B:
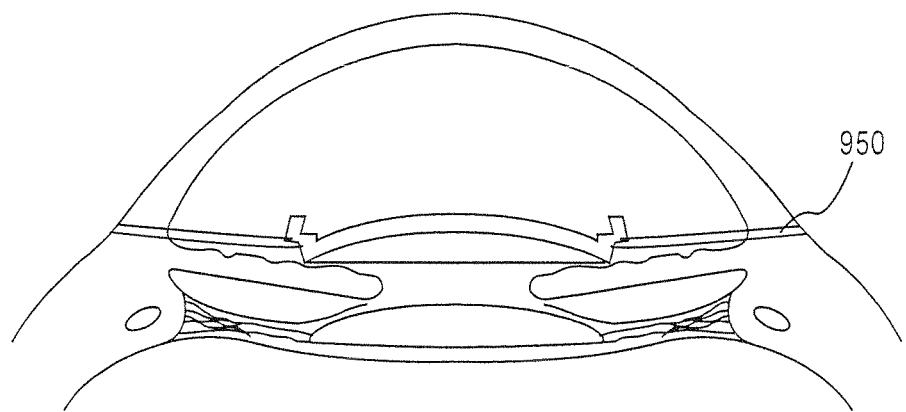
FIG. 32b is a side view of an intraocular lens implanted within a human eye using the anterior chamber angle as support, wherein a base lens includes a communicating element.

In another aspect of the present invention, any of the base lenses described in this application may further comprise a communicating element 950 through which the above-described pharmacological agents may be delivered to replenish a base lens once the pharmacological agent has been exhausted. As shown in FIGS. 32*a* and 32*b*, the communicating element 950 has a lumen, a first end that is in communication with a base lens and a second end that communicates with a space outside the thick wall of the eye (sclera), but covered by the thin outer layer of the eye (conjunctiva). The communicating element 950 extends from the base lens and through the thick eye wall. With this structural arrangement, when the base lens needs to be replenished with pharmacological agent, a surgeon need only insert a needle through the communicating element 950 and inject pharmacological agent into the base lens via the communicating element 950. Thus, an additional supply of pharmacological agents can be supplied without the patient having to endure additional invasive surgery to replace the base lens.

As shown in FIGS. 32a and 32b is it is within the scope of the invention that the base lens and the communicating element 950 be provided in an anterior or posterior position. FIG. 32a shows the base lens placed in a posterior position in the sulcus. FIG. 32b shows the base lens placed in an anterior position in the anterior chamber. In both cases, the communicating element 950 extends through the wall of the eye. Furthermore, while the communicating element 950 is shown as being a substantially tubular channel, the communicating element 950 can be of any shape or extend at any angle suitable to allow a surgeon to use the communicating element 950 to deliver additional pharmacological agents to the base lens. While the aspect illustrated in FIGS. 32a and 32b only show a base lens, it is within the scope of the invention that the base lens may accommodate any one of the front lens assemblies described above.

As described above, the known intraocular lens assemblies may include a mid lens (20, 200, 200', 200", 2000) and a top lens (30, 300, 300', 300", 3000) forming a front lens assembly, or simply a single front lens (20000), which mate with a base lens (10, 100, 100", 1000). Generally, in known intraocular lens assemblies, the base lens contains the bulk of the optical power, while the front lens/optical lens assembly serves the function of fine tuning the optical power. In a preferred aspect of present invention, however, the optical power of the base lens is divided between the base lens and the front lens/optical lens assembly. In a preferred aspect the power is divided evenly between the front lens/optical lens assembly and the base lens. The degree of power of a lens directly correlates to the thickness of the lens. By dividing the power evenly between the lenses, the base lens will be thinner relative to the base lens of the above-described intraocular lens systems. Because the size of the base lens is thinner, the incision required to implant the MC-IOL in the eye may be smaller than the incision required for implanting the known MC-IOLs. By dividing the power between the front lens assembly and the base lens, thereby decreasing the size of the base lens, a smaller incision may be used, which results in less invasive surgery and faster recovery for the patient. Furthermore, it is within the scope of the invention that if multiple lenses are used, as described above and shown in FIG. 27A-27D, the power may be divided between some or all of the additional lenses. However, because the incision size is limited by other factors, such as the size of the instruments, for example, it is preferable that the power be divided between two lenses.

As above-described, the intraocular lens assembly of FIGS. 12A, 12B, 21 and 24 include flanges 105, 1005. The flanges allow the projections or haptics 210, 2100 to mate with corresponding slots 110, 1110. In the disclosed embodiments, the base lens 100, 1000 includes the flanges 105, 1005.

Figure 33A:
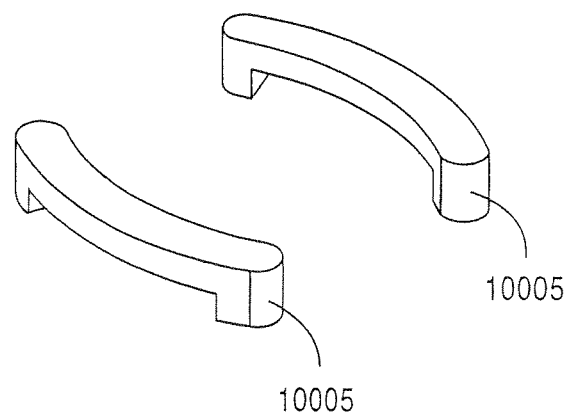
FIG. 33a is a perspective view of a flange according to one aspect of the present invention.
Figure 33B:
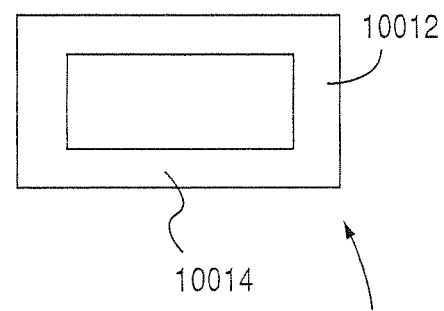
FIG. 33b is a front view of an alternative flange according to another aspect of the present invention.
Figure 33C:
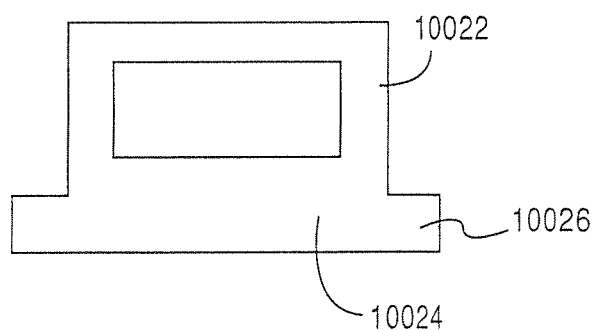
FIG. 33c is a front view of a second alternative flange according to another aspect of the present invention.

As shown in FIG. 33a, in a preferred aspect of the present invention, the flanges 10005 are separate pieces capable of being mountingly engaged to any base lens. The method of attaching the flanges 10005 to a base lens may be achieved by any means known in the relevant art. For example, the flanges may be attached by adding a fixing element such as a medical adhesive to the bottom mating surface of the flanges or to the top mating surface of the base lens, by using lens materials that have adhesive properties, by fusing the materials together or by mechanical means such as a dowel rod/hole mating arrangement, or any equivalent thereof. The flanges 10005 may be attached to any base lens. In an aspect, the flanges 10005 may be attached to an accommodating base lens. An accommodating base lens is a lens that mimics the natural power-changing quality of a natural human eye. An example of an accommodating base lens is described in U.S. Pat. No. 7,601,169. For example, by attaching the flanges 10005 to an accommodating base lens, any of the above-described optical lens assemblies may then be mated with the already implanted base lens. Once the flanges 10005 have been retrofitted on the base lens, the flanges 10005 will project in front of the capsule. Thus, existing base lenses may be retrofitted such that the front lens assemblies described above may be attached thereto FIG. 33b illustrates an alternative flange 10010 that is also capable of being mountingly engaged to any base lens. The flange 10010 is similar to flange 10005 illustrated in FIG. 33a, with a difference being the flange 10010 includes a supporting arm 10014. As shown in FIG. 33b, the supporting arm 10014 extends between two vertical arms 10012. The supporting arm 10014 is connected to each of the vertical arms 10012 at bottom portion of the vertical arms 10012. Therefore, when mounting the flange 10010 to a base lens, a bottom surface of the supporting arm 10014 will be secured to the base lens instead of directly securing the vertical arms 10012 to the base lens. Similarly, FIG. 33c illustrates a second alternative flange 10020, which also includes a supporting arm 10024. However, as shown in FIG. 33c, the supporting arm 10024 further includes a stepped portion 10026. The stepped portion 10026 is a support member integral with, but having a greater length than, the remaining portions of the supporting arm 10024. As with the aspect of FIG. 33b, the supporting arm 10024 may be mounted to a base lens. The additional thickness and stepped portion 10026 of the flange 10020 provides added support for the engagement of a front lens with the base lens.

Figure 34:
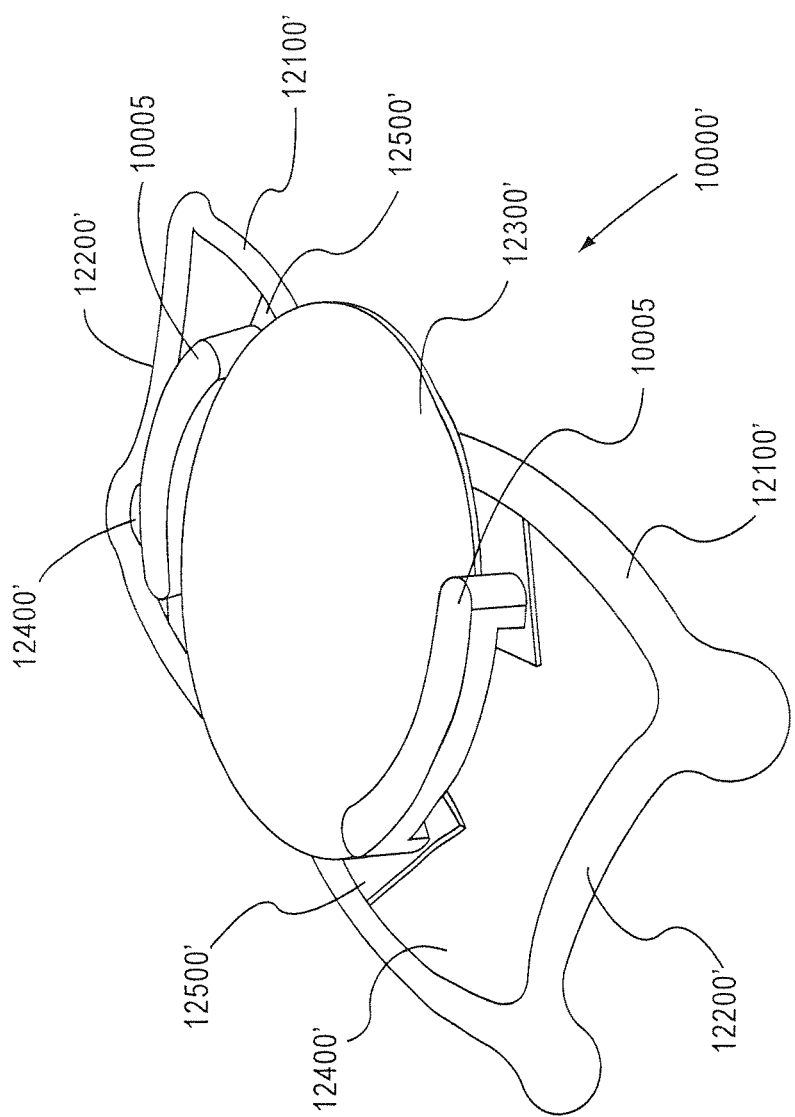
FIG. 34 is a perspective view of an alternative base lens including flanges.

Similarly, in another aspect of the present invention, the flanges 10005, 10010, 10020 may be provided on the haptics on a base lens 10000'. As shown in FIG. 34, the base lens 10000' includes an alternate structure as compared to the base lenses described above. As with the above-described base lenses, the base lens 10000' includes haptics 12000' that extend from the optical portion 12300'. The haptics 12000' of the base lens 10000' are different from the haptics shown in the above disclosed base lenses. For example, as compared to the base lens shown in FIG. 21, the haptics in the base lens 10000' include a first and second set of extending arms 12100', that extend from first and second hemispheres 12300' of the optical portion. First and second connecting elements 12200' joins each arm of the first and second set of extending arms to each other. In this arrangement, as shown in FIG. 34 the two sets of extending arms extend away from each other substantially in opposite directions, such that the base lens is substantially symmetric when cut down a centerline of the optical portion. Thus, the arrangement of the two sets of extending arms, the first and second connecting elements, and the optical portion define first and second apertures 12400'. The haptics of the base lens 10000' further comprise a first and second set of support members 125000'. The support members 12500' are connected to a portion of the extending arms 12100' and along a periphery of the optical portion 12300'. The support members 12500' support the flanges 10005, which are mounted thereon. The flanges 10005 extend orthogonally and allow mating of a front lens assembly with the base lens 10000' in the same manner as described above.

Figure 35A:
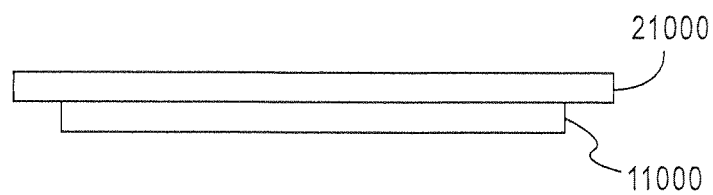
FIG. 35a is a side view of a top lens and base lens having different diameters according to one aspect of the present invention.

The structure of the base lens 10000' has a simpler structure and is easier and cheaper to manufacture than the base lenses discussed above In the above-described aspects, the base lens and the front lens of the optical assembly are shown as having essentially the same geometrical shape and same diameter. In an aspect of the present invention, as shown in FIG. 35a, the single front lens 21000 or the front and mid lens of an optical assembly, have a diameter that is different from the base lens 11000 diameter. By making the lenses have different diameters, the above-described "cellophane wrapping" may be further controlled. In particular, by making the front lens 21000 or the optical lens assembly diameters larger than the base lens 11000 diameter, the "cellophane wrapping" effect is more likely to occur only at the base lens and less likely to occur at the front lens or optical assembly. The "cellophane wrapping" effect only occurring at the base lens desirable because as discussed above, it may be necessary to replace the front lens, which is difficult if the front lens is "cellophane wrapped." On the other hand, the base lens is not typically removed, and therefore, it is desirable to encourage the "cellophane wrapping" effect.

Figure 35B:
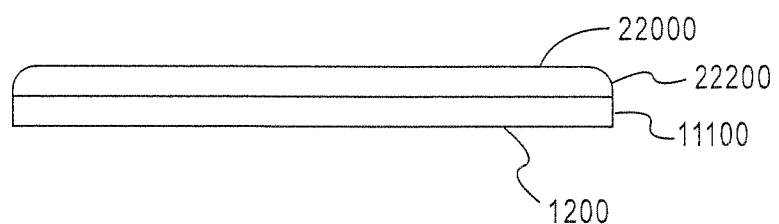
FIG. 35b is a side view of a top lens having rounded edges and base lens having sharp or angular edges according to one aspect of the present invention.
Figure 35C:
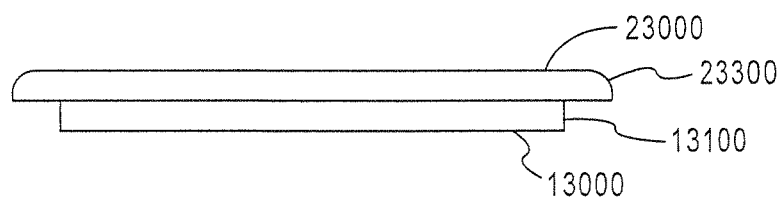
FIG. 35c is a side view of a top lens having rounded edges and a different diameter than a base lens having sharp or angular edges according to one aspect of the present invention.

In another aspect of the present invention, as shown in FIG. 35b, the front lens/optical lens assembly 22000 may have rounded edges 22200 while the base lens 12000 may have sharp or angular edges 11100. The rounded edges curve toward the surface of the front lens 22000. This configuration may be used to further inhibit the cellophane wrapping effect at the front lens assembly and to enhance the effect on the base lens. The wrapping effect is more likely to occur with sharp or angular edges because the capsule has a natural tendency to attach to these shapes. On the other hand, the capsule is less likely to grab a rounded edge. Therefore, by giving the front lens/optical lens assembly rounded edges and the base lens sharp or angular edges, the "cellophane wrapping" effect can further be controlled. In the aspect shown in FIG. 35b, the sharp edge 11100 is a substantially straight vertical edge. It is within the scope of the invention, however, that any degree of sharpness suitable to encourage "cellophane wrapping" may be used. It is also within the scope of the invention that the above-described different diameters may be combined with the edges to further inhibit wrapping of the front lens assembly while encouraging wrapping of the base lens, as shown in FIG. 35c. For example, the front lens 23000 can have rounded edges 23300 and be larger in diameter, while the base 13000 lenses has sharp or angular engages 13100 and a smaller diameter.

As such, the present invention may provide a relatively simple, easy to manufacture and easy to insert intraocular lens implant that provides the patient with a customized optical assembly configured to address the particular needs of the patient's vision.

While the invention has been described in conjunction with regards to specific aspects, it is evident that various changes and modifications may be made, and the equivalents substituted for elements thereof without departing from the true scope of the invention. In addition, many modifications may be made to adapt a particular situation or material to the teachings of the invention without departing from the scope thereof. Therefore, it is intended that this invention not be limited to the particular aspects disclosed herein, but will include all embodiments within the spirit and scope of the disclosure.

What is claimed is:

1. A base lens implantable in an optical system of a human eye, comprising:
   an optical portion;
   a first arm and a second arm extending from a perimeter of the optical portion;
   a first connecting element joining the first arm to the second arm;
   a first aperture defined by the first arm, the second arm, and the first connecting element;
   a first flange at least partially spanning the first aperture; and
   a first support arm extending from the first arm,
   wherein the first flange is connected to a free end of the first support arm.

2. The base lens of claim 1, further comprising a second support arm extending from the second arm, wherein the first flange is connected to a free end of the second support arm.

3. The base lens of claim 2, further comprising:
   a third arm and a fourth arm extending from the perimeter of the optical portion opposite the first and second arms;
   a second connecting arm joining the third arm and the fourth arm;
   a second aperture defined by the third arm, the fourth arm, and the second connecting element; and
   a second flange at least partially spanning the second aperture.

4. The base lens of claim 3, further comprising:
   a third support arm extending form the third arm; and
   a fourth support arm extending from the fourth arm;
   wherein the second flange is connected to the third support arm and connected to the fourth support arm,
   wherein the first support arm is connected to the first arm, the second support arm is connected to the second arm, and the first and second support arms extend into the first aperture, and
   wherein the third support arm is connected to the third arm, the fourth support arm is connected to the fourth arm, and the third and fourth support arms extend into the third aperture.

5. The base lens of claim 4, wherein the first flange comprises a first vertical arm having a lower end connected to a free end of the first support arm, a second vertical arm having a lower end connected to a free end of the second support arm, and a first horizontal arm extending between an upper end of the first vertical arm and an upper end of the second vertical arm to connect the first and second vertical arms, wherein the second flange comprises a third vertical arm having a lower end connected to a free end of the third support arm, a fourth vertical arm having a lower end connected to a free end of the fourth support arm, and a second horizontal arm extending between an upper end of the third vertical arm and an upper end of the fourth vertical arm to connect the third and fourth vertical arms.

6. The base lens of claim 5, wherein the first horizontal arm spans a portion of the first aperture located between the free ends of the first and second support arms, and wherein the second horizontal arm spans a portion of the second aperture located between the free ends of the third and fourth support arms.

7. A multi-component intraocular lens implantable in an optical system of a human eye having:
   a base lens and an optical assembly which engages the base lens, the optical assembly including a front lens and a mid lens having a collar portion,
   wherein the front lens engages the mid lens via the collar portion, the collar portion being provided on a surface of the front lens,
   the multi-component intraocular lens comprising:
   an access bore defined in and extending through an upper end of the collar portion, an outer radial portion of the front lens and the mid lens, and a lower portion of the mid lens to an abutting region defined between the mid lens and the base lens.

8. The multi-component intraocular lens of claim 7, wherein the access bore is sized to receive an ocular surgical needle.

9. A base lens implantable in an optical system of a human eye, comprising:

an optical portion;

a first arm and a second arm extending from a perimeter of the optical portion;

a first connecting element joining the first arm to the second arm;

a first aperture defined by the first arm, the second arm, and the first connecting element;

a first flange extending approximately in an orthogonal direction relative to a direction of extension of the first arm and the second arm; and a second aperture defined by the first flange, wherein the first aperture is in communication with the second aperture.

10. The base lens of claim 9, further comprising a first support arm extending from the first arm, wherein the first flange is connected to a free end of the first support arm.

11. The base lens of claim 10, further comprising a second support arm extending from the second arm, wherein the first flange is connected to a free end of the second support arm.

12. The base lens of claim 11, further comprising:

a third arm and a fourth arm extending from the perimeter of the optical portion opposite the first and second arms;

a second connecting arm joining the third arm and the fourth arm;

a third aperture defined by the third arm, the fourth arm, and the second connecting element;

a second flange extending approximately in an orthogonal direction relative to a direction of extension of the third arm and the fourth arm; and a fourth aperture defined by the second flange, wherein the third aperture is in communication with the fourth aperture.

13. The base lens of claim 12, further comprising:

a third support arm extending form the third arm; and a fourth support arm extending from the fourth arm;

wherein the second flange is connected to the third support arm and connected to the fourth support arm, wherein the first support arm is connected to the first arm, the second support arm is connected to the second arm, and the first and second support arms extend into the first aperture, and wherein the third support arm is connected to the third arm, the fourth support arm is connected to the fourth arm, and the third and fourth support arms extend into the third aperture.

14. The base lens of claim 13, wherein the first flange comprises a first vertical arm having a lower end connected to a free end of the first support arm, a second vertical arm having a lower end connected to a free end of the second support arm, and a first horizontal arm extending between an upper end of the first vertical arm and an upper end of the second vertical arm to connect the first and second vertical arms, wherein the second flange comprises a third vertical arm having a lower end connected to a free end of the third support arm, a fourth vertical arm having a lower end connected to a free end of the fourth support arm, and a second horizontal arm extending between an upper end of the third vertical arm and an upper end of the fourth vertical arm to connect the third and fourth vertical arms.

15. The base lens of claim 14, wherein the first horizontal arm spans a portion of the first aperture located between the free ends of the first and second support arms, and wherein the second horizontal arm spans a portion of the second aperture located between the free ends of the third and fourth support arms.

* * * * *